US007521468B2

(12) United States Patent
Rosenfeld et al.

(10) Patent No.: US 7,521,468 B2
(45) Date of Patent: *Apr. 21, 2009

(54) COMPOUNDS FOR USE IN WEIGHT LOSS AND APPETITE SUPPRESSION IN HUMANS

(75) Inventors: Mark J. Rosenfeld, Draper, UT (US); Scott R. Forsberg, Mountain Green, UT (US)

(73) Assignee: Seroctin Research & Technology, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/385,415

(22) Filed: Mar. 21, 2006

(65) Prior Publication Data

US 2006/0223796 A1 Oct. 5, 2006

Related U.S. Application Data

(62) Division of application No. 10/718,232, filed on Nov. 20, 2003.

(51) Int. Cl.
*A61K 31/42* (2006.01)
*A61K 36/899* (2006.01)

(52) U.S. Cl. .................. 514/376; 514/374; 514/375; 514/909; 424/750

(58) Field of Classification Search .................. 514/376, 514/374, 375, 909
See application file for complete search history.

(56) References Cited

U.S. PATENT DOCUMENTS

| | | | |
|---|---|---|---|
| 3,862,180 A | 1/1975 | Jernow et al. | |
| 3,882,107 A | 5/1975 | Murase et al. | |
| 4,457,872 A | 7/1984 | Murase et al. | |
| 4,558,060 A | 12/1985 | Caignard et al. | |
| 4,778,792 A | 10/1988 | Lesieur et al. | |
| 4,960,778 A | 10/1990 | Lesieur et al. | |
| 5,071,863 A | 12/1991 | Ito et al. | |
| 5,112,843 A * | 5/1992 | Bjostad et al. | 514/375 |
| 5,147,883 A | 9/1992 | Aichaioui et al. | |
| 5,179,091 A | 1/1993 | Lesieur et al. | |
| 5,182,278 A | 1/1993 | Lesieur et al. | |
| 5,196,434 A | 3/1993 | Taverne et al. | |
| 5,240,919 A | 8/1993 | Yous et al. | |
| 5,292,735 A | 3/1994 | Sugimoto et al. | |
| 5,296,477 A | 3/1994 | Taverne et al. | |
| 5,300,507 A | 4/1994 | Yous et al. | |
| 5,322,843 A | 6/1994 | Yous et al. | |
| 5,322,849 A | 6/1994 | Yous et al. | |
| 5,326,775 A | 7/1994 | Yous et al. | |
| 5,386,034 A | 1/1995 | Yous et al. | |
| 5,436,348 A | 7/1995 | Yous et al. | |
| 5,688,820 A | 11/1997 | Mouithys-Mickalad et al. | |
| 5,786,367 A | 7/1998 | Oshiro et al. | |
| 5,919,784 A | 7/1999 | Lesieur et al. | |
| 6,177,422 B1 | 1/2001 | Belliotti et al. | |
| RE37,478 E | 12/2001 | Strupczewski et al. | |
| 6,331,660 B1 | 12/2001 | Chomet et al. | |
| 6,667,308 B2 | 12/2003 | Rosenfeld et al. | |
| 2004/0038909 A1 | 2/2004 | Chawan | |

FOREIGN PATENT DOCUMENTS

| | | |
|---|---|---|
| CH | 683593 | 4/1994 |
| DE | 670 584 | 1/1939 |
| EP | 0070016 A1 | 1/1983 |
| EP | 0478446 | 4/1992 |
| EP | 0 506539 | 9/1992 |
| EP | 0506539 | 9/1992 |

OTHER PUBLICATIONS

Tseng, "Concentration of DIMBOA in leaf tissues at various stages of corn plant in relation to resistance of host plant to the Asian corn borer", Zhiwu Baohu Xuehui Huikan, Vol. 31, No. 1, pp. 34-43 (1989), see the enclosed abstract.*
Garcia H.L., "Dermatological complications,"PuBMed Abstr. 12180897; *American Journal of Clinical Dermatology*, 3(7); 497-506, 2002.
Lee, HS., "Tyrosinase inhibitors of Pulsatilla cernua root-derived materials," PubMed Abstr. 11879010, *Journal of Agricultural Food Chemicals*, 50(6): 140, 2002.
Pischon et al., "Recent developments in the treament of obesity," PuBMed Abstr. 12187313, *Current Opinions of Nephrological Hypertension*, 11(5): 497-502, 2002.
Wang et al., "Hypotensive activity of the pineal indoleamine hormones melatonin, 5-methoxytryptophol and 5-methoxytryptamine," PubMed Abstr. 10752670, *Pharmacological Toxicology*, 86(3): 125-8, 2000.
Katz et al., "Central obesity, depression and the hypothalamo-pituitary-adrenal axis in men and postmenopausal women, " *International Journal of Obesity Related Metabolism Disorders*, 24: 246-51, 2000.
McGahuey et al., "The Arizona Sexual Experience Scale (ASEX): reliability and validity, " *Journal of Sex & Marital Therapy*, 26: 25-40, 2000.
Griffen et al., "Selective serotonin reuptake inhibitors directly alter activity of neurosteroidogenic enzymes," *Proceedings of Natural Academy Sciences* (Washington D.C.), 96(23): 13512-13517, 1999.

(Continued)

*Primary Examiner*—Kevin E Weddington
(74) *Attorney, Agent, or Firm*—Workman Nydegger

(57) ABSTRACT

Phenolic compounds with a phenolic molecule to which are covalently linked an oxygen-containing group, a nitrogen or another oxygen containing group, and a $C_1$-$C_4$ alkoxy group, obtainable from monocotyledonous plants, or by chemical synthesis, have been found to act as weight loss agents, appetite suppressants, mood enhancers and adjunctive therapy for arthritis, sleep apnea, fibromyalgia, diabetes and hyperglycemia. Additional chemical compounds of the present invention may include benzoxazinoids-cyclic hydroxyamic acids, lactams, and corresponding glucosides, which may serve as precursors to phenolic compounds. The phenolic compounds and precursors of phenolic compounds of the present invention, at concentrations suitable for human therapeutic use, may be obtained from monocotyledonous plants such as corn in their early growth states which are timely harvested for optimum yield.

31 Claims, No Drawings

OTHER PUBLICATIONS

Rudolf et al., "Subjective quality of life in female in-patients with depression: A longitudinal study," *International Journal of Social Psychiatry*, 45(4): 238-46, 1999.

Negus et al., "Reproductive strategies of *Dicrostonyx groenlandicus* and *Lemmus sibiricus* in high-arctic tundra," *Canadian Journal of Zoology*, 76: 391-399, 1998.

Gianoli et al., "Characteristics of hydroxamic acid induction in wheat triggered by aphid infestation," *Journal of Chemical Ecology*, 23(12): 2695-2705, 1997.

Niemeyer et al., "Chromosomal location of genes for hydroxamic acid accumulation in *Triticum aestivum* L. (wheat) using wheat aneuploids and wheat substitution lines," *Heredity*, 79: 10-14, 1997.

Dowd et al., "Enzymatic oxidation products of allclochemicals as a basis for resistance against insects: effects on the corn leafhopper *Dalbulus maidis*," *Natural Toxins*, 4: 85-91, 1996.

Cooksey, C., "A Simple One Pot Reaction of 4-Alkoxy and 4-Alkylthio-Catechols and O-Benzoquinones", *Organic Preparations and Procedures Int.*, vol. 28, No. 4, 463-467, 1996.

Meek et al., "Interation of maternal photoperiod history and food type of growth and reproductive development of laboratory meadow voles (*Microlus pennsylvanicus*)," *Physiology and Behavior*, 57(5): 905-11, 1995.

Bergvinson et al., "Putative role of photodimerized phenolic acids in maize resistance to *Ostrinia Nubilalis* (Lepidoptera: Pyralidae)," *Environmental Entomology*, 23(6): 1516-1523, 1994.

Hoshi-Sakoda, M., "Structure Activity Relationships of Enzoxazolinones with Respect to Auxin-Induced Growth and Auxin-Binding Protein", *Phytochemistry*, vol. 37 No. 2, 297-300, 1994.

Hayashi et al., "6-Methoxy-2-benzoxazolinone in *Scoparia dulcis* and its production by cultured tissues," *Phytochemistry*, 37(6): 1611-1614, 1994.

Leighton et al., "Substrate specificity of a glucosyltransferase and an N-hyroxylase involved in the biosynthesis of chyclic hydroxamic acids in Gramineae," *Phlochemistry*, 36(4): 887-892, 1994.

Mayoral et al., "A high performance liquid chromatography method for quantification of DIBOA, DIMBOA, and MBOA from aqueous extracts of corn and winter cereal plants, " *Journal of Liquid Chromatography*, vol. 17, No. 12, pp. 2651-2665, 1994.

Assabgui et al., "Hydroxamic acid content of maize (*Zea mays*) roots of 18 Ontario hybrids and prediction of antibiosis to western corn rootworm, *Diabrotica virgfera virgifera* Leconte (*Cleoptera: Chrysomelidae*)," *Canadian Journal of Plant Science*, 73: 359-363, 1993.

Cuevas et al., "Effect of hydroxamic acids from cereals on aphid cholinesterases," *Phytochemistry*, 34(4): 983-985, 1993.

Frandsen et al., "Maternal transfer of the 6-MBOA chemical signal in *Microtus montarius* during gestation and lactation, "*Canadian Journal of Zoology*, 71: 1799-1803, 1993.

Richardson et al., "Cyclic hydroxamic acid accumulation in corn seedlings exposed to reduced water potentials before, during, and after germination," *Journal of Chemical Ecology*, 19(8): 1613-1624, 1993;* Assabgui et al., "Hydroxamic acid content of maize roots of 18 Ontario hybrids and prediction of antibiosis to western corn rootworm," *Canada Journal of Plant Science*, 73: 359-363, 1993.

Bjostad, Louis B. and Hibbard, Bruce E., "6-Methoxy-2-Benzoxazolinone: a Semiochemical for Host Location by Western Corn Rootworm Larvae," *Journal of Chemical Ecology*, Vol. 18, No. 7, pp. 931-944, 1992.

Arnason et al., "Phototoxins in plant-insect interactions. In Herbivores, Their interactions with secondary plant metabolites," Edited b M. Berenbaum et al., Academic Press, N.Y.; *Ecological and evolutionary processes*, pp. 317-341 vol. II, 2nd Ed., 1992.

Blum et al., "Allelopathic activity in wheat-conventional and wheat-no-till soils: development of soil extract bioassays," *Journal of Chemical Ecology*, 18(12): 2191-2221, 1992.

Givovich et al., "Hydroxamic Acid Glucosides in Honeydew of Aphids Feeding on Wheat," Journal of Chemical Ecology, Vol. 18, No. 6:841-846, 1992.

Nicol et al., "A screen of worldwide wheat cultivars for hydroxamic acid levels and aphid antixenosis," *Annotated Applied Biology*, 121: 11-18, 1992.

Copaja et al., "Hydroxamic acid content of perennial Triticeae," *Phytochemistry*, 30(5): 1531-1534, 1991a.

Copaja et al., "Hydroxamic acid levels in Chilean and British wheat seedlings," *Ann. Applied Biology*, 118: 223-227, 1991b.

Moffatt et al., "Effects of photoperiod and 6-methoxy-2 benzoxazolinone on male-induced estrus in prairie voles," *Physiology and Behavior*, 49: 27-31, 1991.

Xie et al., "Distribution and variation of hydroxamic acids and related compounds in maize (*Zea mays*) root system," *Canadian Journal of Botany*, 69: 677-681, 1991.

Zuniga et al., "Hydroxamic acid content in undifferentiated and differentiated tissues of wheat," *Phytochemistry*, 30(10): 3281-3283, 1991.

Perez et al., "Difference in hydroxamic acid content in roots and root exudates of wheat (*Triticum aestivum* L.) and rye (*Secale cereale* L.): possible role in allelopathy," *Journal of Chemical Ecology*, 17(6): 1037-1043, 1991.

Daya et al., "Effect of 6-methoxy-2-benzoxazolinone on the activities of rat . . . ", *Journal of Pineal Research*, 8:56-66, 1990.

Gower, B.A., "Endocrine effects of the naturally occurring reproductive stimulant, 6-methoxybenzoxazoline," Ph.D. Thesis, University of Utah, Salt Lake City, Utah, 116 pp., 1990.

Gower et al., "Reproductive responses of male *Microtus montanus* to photoperiod, melatonin, and 6-MBOA," *Journal of Pineal Research*, 8:297-317, 1990.

Nelson et al., "Photoperiod affects reproductive responsiveness to 6-methoxy-2-benzoxazolinone in house mice," *Biology of Reproduction*, 43: 586-91, 1990.

Reid et al., "Resistance of maize germ plasm to European corn borer, *Ostrinia nubilalis*, as related to geographical origin," *Canadian Journal of Botany*, 68: 311-316, 1990.

Urbanski et al., "Influence of photoperiod and 6-methoxybenzoxazolinone on the reproductive axis of inbred LSH/Ss Lak male hamester," *Journal of Reproduction and Fertility*, 90: 157-162, 1990.

Niemeyer et al., "Changes in hydroxamic acid levels of wheat plants induced by aphid feeding," *Phytochemistry*, 28(2): 447-449, 1989.

Rowsemitt et al., "Reproductive function in *Dipodomys ordii* stimulated by 6-methoxybenzoxazolinone," *Journal of Mammology*, 70(4): 805-809, 1989.

Butterstein et al., "The plant metabolite 6-methoxybenzoxazolinone interacts with follicle-stimulating hormone to enhance ovarian growth," *Biology of Reproduction*, 39: 465-71, 1988.

Campos et al., "Toxicity and toxicokinetics of 6-methoxybenzoxazolinone (MBOA) in the European corn borer *Ostrinia nubilalis* (Hubner)," *Journal of Chemical Ecology*, 14(3): 989-1002, 1988.

Schadler et al., "The plant metabolite, 6-methoxybenzoxazolinone, stimulates an increase in secretion of follicle-stimulating hormones and size of reproductive organs in *Microtus pinetorum*," *Biology of Reproduction*, 38:817-820, 1988.

Sweat et al., "Uterotropic 6-methoxybenzoxazolinone is an adrenergic agonist and melatonin analog," *Molelcular Cellular Endocrinology*, 57: 131-138, 1988.

Anderson et al., "Effects of melatonin and 6-methoxybenzoxazolinone on photoperiodic control of testis size in adult male golden hamseters," *Journal of Pineal Research*, 5: 351-65, 1988.

Vaughan et al., "Hormonal consequences of subcutaneous 6-methoxy-2-benzoxazolinone pellets or injections in prepubertal male and female rats," *Journal of Reproduction and Fertility*, 83: 859-66, 1988.

Barnes et al., "Role of benzoxazinones in allelopathy by rye (*Secale cereale* L.)," *Journal of Chemical Ecology*, 13(4): 889-906, 1987.

Brice, C., "The effect of 6-methoxybenzoxazolinone on laboratory mice," Ph.D. Thesis, University of London, London, England, 1987.

Korn et al., "Initiation of breeding in a population of *Microtus townsendii* (Rodentia) with the secondary plant compound 6-MBOA," *Oecologia* (Berl.), 71: 593-596, 1987.

Barnes et al., "Isolation and characterization of allelochemicals in rye herbage," *Phytochemistry*, 26(5): 1385-1390, 1987.

Berger et al., "Effect of 6-methoxybenzoxazolinone on sex ratio and breeding performance in *Microtus montanus*," *Biology of Reproduction*, 1987; 36: 255-260, 1987.

Alibbai, S.K., "Reproductive response of *Gerbillus harwoodii* to 6-MBOA in the Kora National Reserve, Kenya," *Journal of Tropical Ecology*, 2: 377-379, 1986.

Cranford et al., "Stimulation of reproduction in *Peromyscus leuopus* and *P. maniculatus* with 6-MBOA in the field," *Virginia Journal of Science*, 37:240-247, 1986.

Epstein et al., "Dynamics of 6-methoxybenzoxazolinone in winter wheat, Effects of photoperiod and temperature," *Journal of Chemical Ecology*, 12(10): 2011-2020, 1986.

Bronson, F.H., "Mammalian reproduction: an ecological perspective," *Biology of Reproduction*, 32(1): 1-26, 1985.

Brake et al., "Delay of onset of oviposition in pullets promoted by 6-methoxybenzoxazolinone," *Poultry Science*, 64(4): 774-776, 1985.

Butterstein et al., "A naturally occuring plant compound, 6-methoxybenzoxazolinone, stimulates reproductive responses in rats," *Biology of Reproduction*, 32: 1018-1023, 1985.

Yuwller et al., "Effects of 6-methoxy-2-benzoxazolinone on the pineal melatonin generating system," *Journal of Pharmacological Exp. Ther.*, 233: 45-50, 1985.

Nachman, R.; "Convenient Preparation of 2-Benzoxazolinones with 1,1-Carbonyldiimidazole", *J. Heterocyclic Chemistry*, vol. 19, 1545-1547, 1982.

Gomita et al., "Behavioral and EEG effects of coixol (6-methoxybenzoxazolinone), one of the components on Coix Lachryma-Jobi L. var. may-yen Stapf," *Nippon Yakurigaka Zasshi*, 77(3): 245-59, 1981.

Argandona et al., "Effect of content and distribution of hydroxamic acids in wheat on infestation by the aphid, *Schizaphis graminum*," *Phytochemistry*, 20(4): 673-676, 1981.

Berger et al., "Chemical triggering of reproduction in *Microtus montanus*," *Science* (Washington D.C.), 214(4516): 69-70, 1981.

Sanders et al., "6-methoxybenzoxazolinone: A plant derivative that stimulates reproduction in Microtis montanus," *Science* (Washington D.C.), 214(4516): 67-69, 1981.

Argandona et al., "Role of hydroxamic acids in the resistance of cereals to aphids." *Phytochemistry*, 19: 1665-1668, 1980.

Arient J., "2-Styryl Benzoxazole Derivatives", *Collection Czechoslov Chem Commun.*, vol. 45, 3160-3165, 1980.

Negus et al., "Experimental triggering of reproduction in a natural population of *Microtus montanus*," *Science* (Washington D.C.), 196(4295): 1230-1231, 1977.

Rindone, B., "Oxidation of Aromatic Anils with Lead Tetra-Acetate", *Journal of the Chemical Society Perkin Trans I*, 2022-2025, 1975.

Calder, I.C., "N-Hydroxylation of P-Acetophenetidide as a Factor in Nephrotoxicity", *Journal of Medicinal Chemistry*, vol. 16, No. 5, 499-502, 1973.

Virtanen et al., "Precursors of benzoxazolinone in rye plants. I. Precursor II, the Agylcone," *Acta Chemica Scandinavica*, 14(2): 499-502, 1960.

Lerosen, A.L., "The Migration of Acetyl and Benzoyl Groups in O-Aminophenol", *Journal of the American Chemical Society*, vol. 70, 2705-2709, 1948.

Pollard, C.B., Acyl Derivatives of Ortho-Amino Phenol:, *Journal of American Chemical Society*, vol. 53, 996-1001, 1931.

Epstein et al., "Dynamics of 6-Methoxybenzoxazolinone in Winter Wheat," *Journal of Chemical Ecology* Vol. 12, No. 10, pp. 2011-2021; and.

Rosenblatt, D.H., "An Anomalous Result of an Attempted Dakin Reaction", *Journal of American Chemical Society*, Vol. 75, 4607-4608.

Ortego, F. et al., "Effect of DIMBOA on Growth and Digestive Physiology of Sesamia nonagrioides (Ledidoptera: Noctuidae) Larvae," J. Insect Physiol., Vol. 44 No. 2, pp. 95-101, 1998.

Berger, et al., Effect of 6-Methoxybenzoxazolinone on Sex Ratio and Breeding Performance in Microtus Montanus, Biol. Repod, 36(2):255-260 (1987).

Epstein, et al. Dynamics of 6-Methoxybenzoxazolinone in Winter Wheat, J. of Chem. Ecol, vol. 12, No. 10, (1986).

*Seroctin Research & Technologies, Inc.* v. *Unigen Pharmaceuticals, Inc. et al.* In the United States District Court, For the District of Utah, Central Division, Case No. 2:07CV582, pleading entitled "Defendant's Preliminary Invalidity Contentions".

* cited by examiner

COMPOUNDS FOR USE IN WEIGHT LOSS AND APPETITE SUPPRESSION IN HUMANS

RELATED APPLICATION

This divisional application claims the benefit of U.S. patent application Ser. No. 10/718,232, filed Nov. 20, 2003, which claims priority to U.S. patent application Ser. No. 09/834,592, filed Apr. 13, 2001, and entitled "NOVEL COMPOUNDS FOR USE AS ANTIDEPRESSANTS, APHRODISIACS AND ADJUNCTIVE THERAPIES IN HUMANS", now issued as U.S. Pat. No. 6,667,308, which claims the benefit of U.S. provisional patent application Ser. No. 60/196,829, filed Apr. 13, 2000, and entitled "ANTIDEPRESSANT, APHRODISIAC, WEIGHT-LOSS AIDE, THERAPY FOR QUITTING NICOTINE OR ADDICTIVE DRUGS AND TREATMENT OF BETTERING REPRODUCTION IN HUMANS", which are incorporated herein by reference.

BACKGROUND

1. Field of the Invention

This invention relates to compositions and methods to induce weight loss, appetite suppression and as adjunctive therapies for fibromyalgia, sleep apnea, diabetes, hyperglycemia and arthritis and more particularly, to novel compositions of phenolic and indoleamine-like compounds which are obtainable in concentrations and amounts suitable for human use from certain botanicals or from chemical synthesis, together with methods for using, producing and harvesting same.

2. The Background Art

An estimated 35-40 million living Americans will suffer major depressive episodes, and many more will experience lesser bouts. Of the approximately 17.5 million Americans with ongoing depressions, about 9.2 million are at a clinically debilitating level. Clinical depression is characterized by a list of symptoms that last over a long time span. It is a serious problem that is usually or initially caused by outside stressors. As stresses escalate or persist, a chemical imbalance can result. Clinical depression can be very debilitating both physically and mentally and even lead to death by means of suicide. However, lost productivity and relationship problems are also consequences of lesser depressions. At present, antidepressant medications are the cornerstones of treating depression, especially those that are at least moderately severe. Although depressed people tend to improve when treated with antidepressants, many do not respond to the first one. Such individuals may eventually benefit from a different antidepressant or a combination of antidepressants.

Sexual dysfunction is a pervasive disorder. In the overall population, 43 percent of women and 31 percent of men between the ages of 18 and 59 repeatedly experience it. Sexual dysfunction includes lacking interest in sex, problems with arousal, not enjoying sex, and anxiety about sexual performance. Indeed, feeling good in general has significant impact on sexual function, with those people unhappy or depressed more likely to experience difficulties. Arousal problems affect over 20 million American males, about two in 10 adult men, with such difficulties often associated with or accompanied by some sort of depression. Meanwhile, prescription antidepressants actually exacerbate the situation, since a frequent side effect of their use is sexual dysfunction. In fact, sexual response diminishes in up to 75% of prescription antidepressant users.

There is a need for treatments to reduce depression or otherwise better mood with an accompanying enhancement of sexual response or desire, or at least no sexual dysfunction.

Prior work on the compounds of the invention has solely been on 6-methoxy-2,3-benzoxazolinone (6-MBOA). Its role in strengthening the resistance of monocotyledonous plants against a wide range of insect pests has been much studied. 6-MBOA and its chemical precursors also have allelopathic properties that inhibit root and shoot growth in competing species. Furthermore, it has antimicrobial properties. 6-MBOA appears constitutively during early stages of growth, localized in those tissues most exposed to microbial and insect attack.

It had been long suspected that compounds in plants affect the seasonal reproductive output of wild rodents. In 1981, 6-MBOA became the first naturally occurring compound in a plant verified as impacting seasonal reproductive cycling. Since then, a substantial body of work has accumulated on 6-MBOA as an initiator of seasonal breeding and an effector of population size for many rodents and a few birds. Compounds related to and possibly co-occurring with 6-MBOA remain unexplored in this regard.

Excessive weight (i.e., overweight) and obesity are part of the most rapidly growing public health concerns facing the world today. By the end of the 1980s, nearly one-fourth of Americans were overweight (a Body Mass Index (BMI) greater than 25, calculated as weight in kilograms/height in meters squared; Calle et al., "Body mass index and mortality in a prospective cohort of US adults", *New England Journal of Medicine* 341:1097-1105, 1999) or obese (excess body weight more than 20 percent above average for height, bone structure and age, or a BMI exceeding 30). The number of overweight children has nearly tripled over the previous 20 years; and, the prevalence and incidence of type 2 diabetes, a disease for which obesity is a major factor, in adolescents has significantly increased over the same time. By 1999, about thirty-six percent (36%) of the total population, or more than 97,000,000 adults, may be considered overweight. Currently, it has been estimated that about sixty percent (60%) of Americans are overweight and about thirty percent (30%) of Americans may be considered obese.

Obesity has a similar epidemic pattern in Europe, and in 2002 it was estimated that more than 200 million people (about thirty-three percent (33%)) of the population could be considered overweight. In many European countries more than fifty percent (50%) of adults are now overweight, nearly triple the level prior to 1980. Germany has the most overweight men in Europe, with an incidence of seventy-one percent (71%). The United Kingdom is not far behind Germany with excess weight in more than sixty percent (60%) of the adult population.

Overweight and obesity are commonly associated with other serious health conditions. These conditions may be causes of increased morbidity in overweight and obese individuals. These serious health conditions and obesity are often referred to as being "co-morbid." Being overweight is known to increase the risk of dying from many conditions, including 4 of the 10 leading causes of death: coronary heart disease, cancer, stroke and type 2 diabetes. Some epidemiological information suggests increases in mortality tend to parallel increases in body weight. In the United States, being overweight has become the second leading cause of preventable, premature death, with the associated annual loss of life exceeding 2,800,000 people (Allison et al., "Annual deaths attributable to obesity in the United States", Journal of the American Medical Association 282:1530-1538, 1999).

Excessive weight and/or obesity may be due to uncontrollable and/or controllable factors. Uncontrollable factors may include heredity (i.e., genetics) and metabolic disorders. Controllable factors may include environment, physical inactivity, psychological circumstances, and poor eating habits established in childhood. Poor eating habits may include excessive intake as well as poor selection of foods with nutritional value. The controllable factors are often more responsible for the development of overweight and obesity.

Therapeutic approaches to overweight and obesity have included educational, physical, psychological and pharmacological modalities. Educational efforts have focused on informing individuals about caloric intake and making proper nutritional selections. Physical approaches have emphasized increasing physical activity in an effort to increase metabolism. Psychological approaches have focused on controlling appetite, manipulating mood and improving sense of well-being. Pharmacological approaches may include drugs and other agents to suppress appetite and/or increase cellular metabolism. There are a broad range of opinions as to how successful these therapeutic approaches have been either individually or collectively, but nevertheless, incidence and prevalence of overweight and obesity continue to increase. Regardless of cause, there is obvious need for treatments that can induce or otherwise promote weight loss.

Medications prescribed for losing weight often suppress appetite by way of mood enhancing attributes (Halpern et al., "Treatment of obesity. An update on anti-obesity medications", *Obesity Reviews* 4:25-42, 2003) and may include, beta-phenethylamine derivatives (fenfluramine, phentermine, phendimetrazine, diethylpropion, and sibutramine); tricyclic derivatives (mazindol); a naftilamine derivative (sertraline); phenylpropanolamine derivatives (ephedrine, phenylpropanolamine); and a phenylpropanolamine oxytrifluorphenyl derivative (fluoxetine).

Ethnobotanists, pharmacognosists and medicinal chemists are constantly in search of new compounds from plant materials that have mood enhancing properties and possible therapeutic roles in weight loss. It had been long suspected that compounds in some plants effect the mood of wild rodents. These effects are sometimes examined by observing seasonal reproductive output. In 1981, 6-methoxy-2,3-benzoxazolinone (6-MBOA) became the first naturally occurring compound in a plant verified as impacting seasonal reproductive cycling. 6-MBOA may be found in varying concentrations in monocotyledonous plants. Since its discovery, a substantial body of work has accumulated on 6-MBOA as an initiator of seasonal breeding and an effector of population size for many rodents and a few birds.

6-MBOA is passed from adult females to offspring during gestation and lactation, with increased growth and larger gonads in the recipient young. Juveniles rely on the interaction of maternal photoperiod history and 6-MBOA to time the onset of growth and puberty. Adults fed a diet containing 6-MBOA produce more female progeny. When 6-MBOA is fed to pregnant females, gonadal development in the male offspring is enhanced.

For rodents, the inhibitory effects of melatonin on growth and reproduction are blocked partially by 6-MBOA (Gower et al., "Reproductive responses of male Microtus montanus to photoperiod, melatonin, and 6-MBOA", *Journal of Pineal Research*, 8: 297-312, 1990). 6-MBOA may obstruct melatonin at the melatonin receptors or act independently to check melatonin action (Sweat et al., "Uterotropic 6-methoxybenzoxazolinone is an adrenergic agonist and melatonin analog, *Molecular and Cellular Endocrinology*, 57:131-138, 1988).

The high melatonin levels induced by 6-MBOA may cause desensitization of melatonin receptors (Daya et al., "Effect of 6-methoxy-2-benzoxazolinone on the activities of rat pineal N-acetyltransferase and hydroxyindole-O-methyltransferase and on melatonin production", *Journal of Pineal Research*, 8:57-66, 1990), but not for all rodents (Anderson et al., "Effects of melatonin and 6-methoxybenzoxazolinone on photoperiodic control of testis size in adult male golden hamsters", *Journal of Pineal Research*, 5:351-65, 1988).

This compound stimulates rather than inhibits melatonin biosynthesis and does not prevent stimulation of melatonin synthesis by norepinephrine (Yuwiler et al., "Effects of 6-methoxy-2-benzoxazolinone on the pineal melatonin generating system. *J. Pharmacol. Exp. Ther.* 233:45-50, 1985). 6-MBOA acts at both the alpha- ($\alpha$-) and beta- ($\beta$-) adrenergic receptors (Daya et al., "Effect of 6-methoxy-2-benzoxazolinone on the activities of rat pineal N-acetyltransferase and hydroxyindole-O-methyltransferase and on melatonin production", *Journal of Pineal Research*, 8:57-66, 1990), and stimulates adenylcyclase activity in the pineal, hypothalmus and pituitary glands (Sweat et al., "Uterotropic 6-methoxybenzoxazolinone is an adrenergic agonist and melatonin analog, *Molecular and Cellular Endocrinology*, 57:131-138, 1988).

Certain responses to 6-MBOA, like uterine hypertrophy, can be duplicated with estrogen, but 6-MBOA is not an estrogenic compound (Gower, "Endocrine effects of the naturally occurring reproductive stimulant, 6-methoxybenzoxazolinone", Ph.D. Thesis, University of Utah, Salt Lake City, Utah, 1990). Also, 6-MBOA increases the rate of synthesis of follicle stimulating hormone (Butterstein et al., "The plant metabolite 6-methoxybenzoxazolinone interacts with follicle-stimulating hormone to enhance ovarian growth", *Biology of Reproduction*, 39:465-71, 1988) and pituitary prolactin (Vaughan et al., "Hormonal consequences of subcutaneous 6-methoxy-2-benzoxazolinone pellets or injections in prepubertal male and female rats", *Journal of Reproduction and Fertility*, 83:859-66, 1988).

Hypothalamic luteinizing hormone-releasing hormone contents and pituitary gland weights are greater for at least one rodent species implanted with capsules containing 6-MBOA (Urbanski et al., "Influence of photoperiod and 6-methoxybenzoxazolinone on the reproductive axis of inbred LSH/Ss Lak male hamsters. *Journal of Reproduction and Fertility*, 90:157-163, 1990). The above studies cumulatively point to 6-MBOA acting in an area of the brain, which may be referred to as the pineal hypothalamic pituitary axis (PHPA), possibly as a melatonin agonist and at the $\alpha$- and $\beta$-adrenergic receptors in its own right. The inventors recognized that 6-MBOA and the indoleamine, melatonin, share a structural similarity. However, melatonin exacerbates symptoms of dysphoria in depressed people. 6-MBOA, as a melatonin agonist, could prove contrary in this regard and actually improve mood. Yet, the inventors are not aware of any prior art that has explored or suggested the use of 6-MBOA and related compounds as having psychotropic effects in humans, particularly with respect to depression or mood.

An object of the invention is to develop therapies for depression and sexual dysfunction entailing use of compounds belonging to related chemical families, of which 6-MBOA is a member. Pursuant to this end, a further object is to develop methods for getting said compounds from plant and animal sources in amounts suitable for human therapeutic use.

While past research by those skilled in the art has attempted to isolate, identify and characterize new plant compounds with mood stimulating properties, 6-MBOA has heretofore previously not been identified or evaluated for mood elevation leading to appetite suppression and weight loss. Therefore, as readily appreciated by those skilled in the art, novel compounds isolated, produced and harvested from monocotyledonous plants and methods for using the same to suppress appetite and promote weight loss in mammals would be a significant advancement in the art. Such novel compositions and methods are disclosed and taught herein.

BRIEF SUMMARY AND OBJECTS OF THE INVENTION

A primary object of the present invention is to provide novel chemical compositions derived, isolated, and/or extracted from monocotyledonous plants or by chemical synthesis, and methods of use to achieve weight loss in mammals.

It is another object of the present invention to provide novel chemical compositions derived, isolated, and/or extracted from monocotyledonous plants or by chemical synthesis, and methods of use to suppress appetite in mammals.

It is also an object of the present invention to provide novel chemical compositions derived, isolated, and/or extracted from monocotyledonous plants or by chemical synthesis, and methods of use to elevate mood in mammals.

It is a further object of the present invention to provide novel chemical compositions derived, isolated, and/or extracted from monocotyledonous plants or by chemical synthesis, which function as melatonin analogs and/or agonists in mammals.

In addition, it is an object of the invention to provide novel methods for growing monocotyledonous plants which results in an increased yield of 6-MBOA and other phenolic and indole-amine compounds.

It is a further object of the present invention to provide novel methods for harvesting monocotyledonous plants which are efficient for producing 6-MBOA and other phenolic and indoleamine compounds.

In addition, it is a further object of the present invention to provide novel chemical compositions derived, isolated, and/or extracted from monocotyledonous plants or by chemical synthesis, and methods of use as adjunctive therapy in fibromyalgia.

It is also an object of the present invention to provide novel chemical compositions derived, isolated, and/or extracted from monocotyledonous plants or by chemical synthesis, and methods of use as adjunctive therapy in sleep apnea.

Additionally, it is an object of the present invention to provide novel chemical compositions derived, isolated, and/ or extracted from monocotyledonous plants or by chemical synthesis, and methods of use as adjunctive therapy in diabetes.

It is a further object of the present invention to provide novel chemical compositions derived, isolated, and/or extracted from monocotyledonous plants or by chemical synthesis, and methods of use as adjunctive therapy in hyperglycemia.

It is a still further object of the present invention to provide novel chemical compositions derived, isolated, and/or extracted from monocotyledonous plants or by chemical synthesis, and methods of use as adjunctive therapy in arthritis. It is also an object of the present invention to provide novel methods for growing and harvesting monocotyledonous plants to obtain phenolic compounds with a phenolic molecule to which are covalently linked an oxygen-containing group, a nitrogen or second oxygen containing group, and at least one $C_1$-$C_4$ alkoxy group.

Additionally, it is an object of the present invention to provide novel methods for promoting weight loss in mammals by administering phenolic compounds with a phenolic molecule to which are covalently linked an oxygen-containing group, a nitrogen or second oxygen containing group, and at least one $C_1$-$C_4$ alkoxy group.

It is a further object of the present invention to provide novel methods for suppressing appetite in mammals by administering phenolic compounds with a phenolic molecule to which are covalently linked an oxygen-containing group, a nitrogen or second oxygen containing group, and at least one $C_1$-$C_4$ alkoxy group.

It is also an object of the present invention to provide novel methods for growing and harvesting monocotyledonous plants to obtain precursors of phenolic compounds comprising benzoxazinoids-cyclic hydroxamic acid, lactams and their corresponding glucosides.

Additionally, it is an object of the present invention to provide novel methods for promoting weight loss in mammals by administering precursors of phenolic compounds comprising benzoxazinoids-cyclic hydroxamic acid, lactams and their corresponding glucosides.

It is a further object of the present invention to provide novel methods for suppressing appetite in mammals by administering precursors of phenolic compounds comprising benzoxazinoids-cyclic hydroxamic acid, lactams and their corresponding glucosides.

Consistent with the foregoing objects, and in accordance with the invention as embodied and broadly described herein, it has been found that certain phenolic compounds and precursors of phenolic compounds, related to each other by shared structural similarities and having structural similarities with melatonin, are effective in bettering mood, improving sexual desire and performance, and as an adjunctive therapy for weight loss and substance abuse and addiction. The novel compounds of the present invention naturally exist as plant secondary metabolites in the early growth of monocotyledonous plants, become concentrated from their ingestion within certain animal parts, or can be synthesized by chemical means. The invention includes therapies using the novel compounds of the present invention for treating depression and sexual dysfunction, as well as adjunctive therapies for achieving weight loss and problems of substance abuse and addiction. The therapeutic method comprises the ingestion of the novel compounds of the present invention over a certain period of time, or other means for getting the compounds of the invention into the body. Both males and females benefit from ingesting the compounds of the invention, while still contained in dried leaves from monocotyledonous plants with such compounds or taken as purified and/or synthesized preparations. It appears that the compounds of the invention act as antidepressants without the undesirable side effects of currently used antidepressants.

As discussed in greater detail hereinbelow, one presently preferred embodiment of the present invention comprises administration of phenolic compounds belonging to related chemical families of which 6-methoxy-2,3-benzoxazolinone (6-MBOA) is a member. These phenolic compounds share a structural similarity with melatonin and indoleamine compound. Based on structural similarities with melatonin, compounds of the invention were studied for their effects on weight loss, appetite suppression and mood properties. In therapeutically effective amounts, novel compounds of the present invention may also be helpful as adjunctive therapies for conditions selected from the group consisting of arthritis, sleep apnea, fibromyalgia, diabetes and hyperglycemia.

In one presently preferred embodiment of a method of the present invention, particular emphasis is placed on promoting weight loss in mammals by the administration of a therapeutically effective amount of a composition of 6-methoxy-2,3-benzoxazolinone or pharmaceutically acceptable salts thereof. In yet another presently preferred embodiment of the present invention, particular emphasis is placed on novel methods of suppressing appetite in mammals by the administration of a therapeutically effective amount of a composition of 6-methoxy-2,3-benzoxazolinone or pharmaceutically acceptable salts thereof.

A source of the novel compounds of the present invention is in monocotyledonous plants in their early growth stages. To obtain these compounds at concentrations suitable for human therapeutic use from such monocotyledonous plants, harvest of these plants at an early life history stage and drying using explicit parameters, as well as specific analytical criteria to ascertain suitability, are employed. However, it is also possible to get the compounds of the invention at concentrations suitable for human therapeutic use from animals parts, including, but not necessarily limited to, the velvet antler tips of deer and elk (*Cervidae*), where they become concentrated after ingestion by the animal of sprouting and otherwise immature grasses. The compounds of the invention can also be obtained through chemical synthesis.

DETAILED DESCRIPTIONS OF THE PREFERRED EMBODIMENTS

It will be readily understood that the components of the present invention, as generally described and illustrated in the formulae and tables herein, could be arranged and designed in a wide variety of different configurations. Those of ordinary skill in the art will, of course, appreciate that various modifications to the details herein may be made without departing from the essential characteristics of the invention, as described. Thus, the following more detailed description of the embodiments of the compositions and methods of the present invention is not intended to limit the scope of the invention, as claimed, but it is merely representative of the presently preferred embodiments of the invention.

Referring to Formulae I-IV, below, the compounds of the invention have in common a phenol molecule to which are covalently linked an oxygen-containing group, a nitrogen- or another oxygen-containing group, and a $C_1$-$C_4$ alkoxy group. Using standard conventions for depicting chemical structures, Formulas I-III disclose the chemical structures and specific parameters defining the compounds of the invention. Formula IV is a unifying formula depicting all compositions of the invention.

Formula I—A chemical composition according to the formula

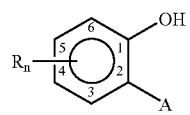

Wherein "R" represents $C_1$-$C_4$ alkoxy, with the proviso that R is in the 4 or 5 ring position;

Wherein "n" represents one of the integers 0, 1 or 2;

Wherein "A" represents —OH, —$NH_2$, or NHCR', where R' represents $C_1$-$C_4$ alkyl;

or pharmaceutically acceptable salts thereof.

Formula II—A chemical composition according to the formula

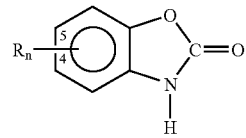

Wherein "R" represents $C_1$-$C_4$ alkoxy, with the proviso that R is in the 5 or 6 ring position;

Wherein "n" represents one of the integers 0, 1 or 2;

or pharmaceutically acceptable salts thereof.

Formula III—A chemical composition according to the formula

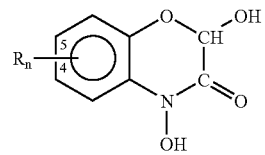

Wherein "R" represents $C_1$-$C_4$ alkoxy, with the proviso that R is in the 6 or 7 ring position;

Wherein "n" represents one of the integers 0, 1 or 2;

or pharmaceutically acceptable salts thereof.

Formula IV—A chemical composition according to the formula

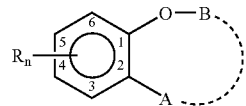

Wherein "R" represents $C_1$-$C_4$ alkoxy, with the proviso that R is in the 4 or 5 ring position;

Wherein "n" represents one of the integers 0, 1 or 2;

Wherein "B" represents H and "A" represents —OH, —$NH_2$, or NHCR', where R' denotes $C_1$-$C_4$ alkyl; and "B A" represents

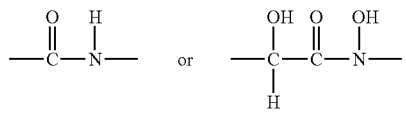

or pharmaceutically acceptable salts thereof.

It has been found that compounds of the invention, when ingested or otherwise introduced into the user's body, are effective for achieving weight loss, suppress appetite, improve mood and appear likewise effective in adjunctive treatment of fibromyalgia, sleep apnea, diabetes, hyperglycemia and arthritis. The term adjunctive therapy is defined as a therapy which is joined or added to the primary therapy, but is not meant to substitute for the primary therapy. The compounds may be administered in the form of ground parts of plants in which they naturally occur, like the ground leaves of immature plants, or as purified or chemically synthesized compounds in a pharmaceutically acceptable carrier.

The compounds of the invention may be administered orally in the form of tablets, capsules, suspensions, solutions or other means suitable for such ingestion, perhaps as an admixture with other compounds to enhance absorption into the blood stream or to otherwise assist in achieving the desired effects. Likewise, oral administration is contemplated to include sublingual (i.e., under the tongue) dosage forms. The compounds of the invention may also be delivered by intranasal (i.e., through the nasal structures) or transmucosal (i.e., across mucous membranes) administration.

The compounds of the invention may also be administered parenterally, as a subcutaneous, intramuscular or intravenous injection, or by way of an implant for sustained release. When administered parenterally, the compounds of the invention are to be dissolved in physiologically acceptable liquid media and/or otherwise compounded in accordance with the known pharmaceutical art. Another mode of administering the compounds of the invention may be a transdermal patch, in which entry of the compounds of the invention into the body is facilitated via acceptable and appropriate carrier molecules.

Unless otherwise defined, the technical, scientific and medical terminology used herein has the same meaning as understood by those informed of the art to which this invention belongs.

6-MBOA and related compounds may have actions in an area of the brain, which may be referred to as the pineal hypothalamic pituitary axis (PHPA), as melatonin agonists and at the α- and β-adrenergic cell receptors in their own right. These properties may be considered to indicate desirable psychotropic effects in humans consequent to the administration of 6-MBOA and related compounds. Whereas melatonin exacerbates symptoms of dysphoria in depressed people, 6-MBOA, as a melatonin agonist, works in contrary fashion and actually stimulates a better mood.

There has previously been no suggestion to implicate the administration of 6-MBOA and related compounds as conducive to weight loss and/or appetite suppression. Mood improvement with the compounds of the invention appears to be accomplished through biochemical or physiological pathways different than are those affected by the above mentioned prescription medications. Improved mood typically means that serotonin levels have been somehow raised, and increased amounts of serotonin may impart a feeling of satiety in a mammal. One result of this feeling may be a reduced food intake and there may additionally be a reduction in body weight.

The following examples will illustrate the practice of the present invention in further detail. It will be readily understood by those skilled in the art that the following methods, formulations, and compositions of novel compounds of the present invention, as generally described and illustrated in the Example herein, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Examples 1-7, is not intended to limit the scope of the invention, as claimed, but is merely representative of presently preferred embodiments of the invention.

EXAMPLE 1

The Similar Physiological Effects of the Compounds of the Invention

Representative compounds of Formulas I, II, and III are shown below as compounds 1-7. The compounds of Formulas I, II and III have like physiological properties, and as such may be considered as similar or equivalent for therapeutic purposes, and were tested via a rodent model.

1. 2-amino-5-methoxyphenol [Member of Formula I]

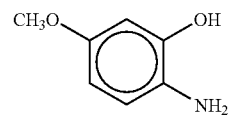

2. 6-methoxy-2-benzoxazolinone [Member of Formula II]

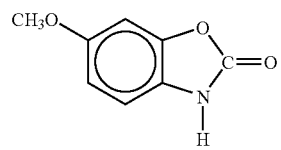

3. 2,4-dihydroxy-7-methoxy-1,4-(2H)-benzoxazin-3-one [Member of Formula III]

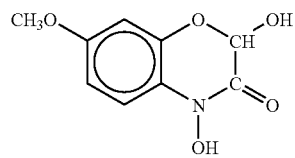

4. 2-hydroxy-4-methoxyacetanilide [Member of Formula I]

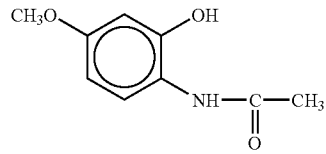

5. 2-hydroxy-4-ethoxyacetanilide [Member of Formula I]

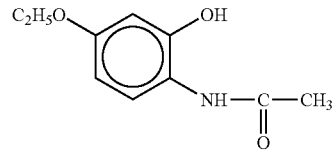

6. 5-methoxy-2-benzoxazolinone [Member of Formula III]

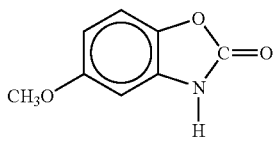

7. 2-hydroxy-5-methoxyacetanilide [Member of Formula I]

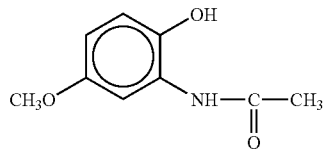

Female montane voles, *Microtis montanus*, received intra peritoneal injections of representative compounds belonging to Formulas I, II and III for three consecutive days and sacrificed twenty-four (24) hours after the last injection to examine uterine weight response. To assess the properties of each representative compound, pure ones made by chemical means (University of Utah Department of Chemistry, Salt Lake City, Utah) were prepared specifically for this test. All compounds were injected at a dose level of 5 mcg/day, dissolved in five percent (5%) propylene glycol for a total injection volume of 0.5 ml. Control animals received 0.5 ml of five percent (5%) propylene glycol only. All voles were 4-5 weeks old and weighed 25-29 g.

As illustrated in Table 1 below, all compounds belonging to Formulas I, II and III caused a statistically significant increase in uterine weights.

TABLE 1

Effect of injecting compounds of the invention, members of Formulas I, II and III on uterine weight in the montane vole, *Microtus montanus*.

| Compound Injected | Formula Numeral | Number of Animals | Average Uterine Weight (mg) |
|---|---|---|---|
| Control (Propylene Glycol) | — | 8 | 15.2 ± 2.4 |
| 6-methoxy-2-benzoxazolinone | II | 11 | 27.7 ± 5.6* |
| 5-methoxy-2-benzoxazolinone | III | 8 | 20.0 ± 4.7** |
| 2-hydroxy-4-methoxyacetanilide | I | 8 | 23.1 ± 2.7* |
| 2-hydroxy-4-ethoxyacetanilide | I | 8 | 22.2 ± 3.9* |
| 2-amino-5-methoxyphenol | I | 8 | 21.8 ± 3.5* |
| 2-hydroxy-5-methoxyacetanilide | I | 8 | 21.1 ± 4.4*** |
| 2-amino-4-methoxyphenol | I | 8 | 22.2 ± 3.2* |

*Significantly different from control at $P < 0.001$
**Significantly different from control at $P < 0.015$
***Significantly different from control at $P = 0.004$ On average, the uterine weight in voles receiving these was 22.8 g, fifty percent (50%) greater than for the control group. The greatest average weight increase, eighty-two percent (82%) more than the uterine weight for the control voles, was in those females administered 6-methoxy-2-benzoxazolinone, but even the least effect of a compound belonging to Formulas I, II or III, that for 5-methoxy-2-benzoxazolinone, entailed a thirty-two percent (32%) increase in uterine weight. The results show that physiological effects or modes of action are held in common by the compounds of the invention.

EXAMPLE 2

Compounds of the Invention as an Antidepressant and Aphrodisiac in Human Males

This component of the invention relates to a method for lessening depression and otherwise bettering mood or feelings of well-being, said method comprising the administration to human males of an effective amount of one or more of the compounds of the invention defined herein. This component of the invention also relates to a method for treating sexual dysfunction or otherwise increasing sexual desire and performance, including but not necessarily limited to lacking interest in sex, problems with arousal, not enjoying sex, and anxiety about sexual performance, said method comprising the administration of an effective amount of one or more of the active compounds of the invention.

A double-blind crossover study was done on human males to test compounds of the invention as a therapeutic agent for treating depression or otherwise elevating mood as well as bettering sexual function. The trial had three phases, each two weeks in duration, during which participants took compounds of the invention for one phase or two weeks. The daily dose was made up from compounds of the invention naturally contained in the ground leaves from immature corn plants, 30-45 cm tall, standardized with synthesized 6-methoxy-2-benzoxazolinone, to a total of 15 mg 6-methoxy-2-benzoxazolinone. A dose of fifteen milligrams (15 mg) was selected because this was considered a likely minimum effective daily amount for humans, extrapolated from prior studies on rodents, rabbits and other animals. Previous anecdotal trials on humans done by the inventors suggested that a 15 mg daily dose had a desirable effect, but no adverse consequences to health. In general, therapeutically effective amounts of compounds of the invention may be found in a daily dosage range of between about 5 micrograms (mcg) to about 60 mg.

Weekly assessments of depression or mental well being and sexual function were done via widely accepted indices: to quantify depression and generalized anxiety disorders, the Hospital Anxiety and Depression Scale (HAD); and for sexual desire, psychological arousal, and overall sexual outlook, the Arizona Sexual Experience Index (ASEX).

Phase One lasted 14 days, during which participants took daily doses of the invention or a placebo. Assignation of the invention or placebo to male participants was done randomly. Immediately prior to the 14 days comprising Phase One, an initial physical examination and blood analysis were done. At that time, each male filled out HAD and ASEX forms to assess mental well being and sexual function, was checked for sitting and standing blood pressure and pulse, and gave the blood sample needed for the biochemical analyses.

Phase Two consisted of a seven-day period immediately after Phase One, during which neither invention nor placebo was taken. During Phase Two, physical examination and laboratory analyses were again done. In Phase Three which lasted 14 days, participants again took either invention or a placebo. Assignation of the invention or placebo was done according to the sort of capsule taken during Phase One. If a participant took a compound of the invention in Phase One, then placebo was administered during Phase Three, and vice versa. Immediately after finishing Phase Three, a physical examination and laboratory analyses were again done. After completing Phase Three, each participant was asked prepared questions as well as solicited for any comments and impressions concerning invention use.

Table 2 is a tabular summary of a presently preferred embodiment of the results that may be observed in Example 2.

TABLE 2

HAD and ASEX summaries for administration of the compounds of invention to adult males.

| Participant | With Compounds of Invention: | | With Placebo: | |
|---|---|---|---|---|
| | Initial Value | After Two-Weeks | Initial Value | After Two-Weeks |
| 1 | 9.0, 12.0 | 8.0, 11.0 | 8.0, 10.0 | 8.0, 13.0 |
| 2 | 16.0, 13.0 | 14.0, 12.0 | 16.0, 13.0 | 16.0, 15.0 |
| 3 | 15.0, 10.0 | 9.0, 11.0 | 15.0, 14.0 | 17.0, 14.0 |
| 4 | 12.0, 9.0 | 7.0, 10.0 | 9.0, 10.0 | 9.0, 12.0 |
| 5 | 14.0, 10.0 | 10.0, 10.0 | 12.0, 10.0 | 14.0, 10.0 |
| 6 | Participant not reliable - Data incomplete and deleted from study | | | |
| 7 | 12.0, 9.0 | 7.0, 9.0 | 9.0, 10.0 | 8.0, 9.0 |
| 8 | 12.0, 11.0 | 8.0, 11.0 | 12.0, 11.0 | 12.0, 10.0 |
| 9 | 12.0, 15.0 | 12.0, 10.0 | 7.0, 10.0 | 7.0, 10.0 |
| 10 | 4.0, 15.0 | 0.0, 13.0 | 9.0, 12.0 | 12.0, 12.0 |
| 11 | 21.0, 10.0 | 6.0, 10.0 | 9.0, 12.0 | 12.0, 12.0 |
| 12 | 13.0, 9.0 | 2.0, 9.0 | 13.0, 9.0 | 13.0, 9.0 |
| 13 | 14.0, 12.0 | 13.0, 10.0 | 12.0, 10.0 | 12.0, 10.0 |
| 14 | 12.0, 10.0 | 13.0, 10.0 | 18.0, 7.0 | 16.0, 7.0 |
| 15 | 23.0, 8.0 | 18.0, 9.0 | 16.0, 9.0 | 16.0, 8.0 |
| Average | 13.5, 10.9 | 9.1, 10.4 | 11.8, 10.5 | 12.3, 10.8 |

The HAD value precedes the ASEX one, and these are separated from each other by a comma. Two-Sample Paired Sign Test - This is one of the stronger or more reliable statistical tests when significance is detected. The question is whether INVENTION affects feelings of well-being or sexual function. The Sign-Test is used to statistically ask "how often compounds of invention impact feelings of well being and/or sexual function". Results are as follows:
HAD (with invention), $p < 0.003$, Very Significant
ASEX (with invention, $p < 0.727$, Not Significant
HAD (with placebo), $p < 0.688$, Not Significant
ASEX (with placebo), $p < 1.310$, Not Significant These data indicate that the compounds of the invention have significant positive effect on depression or mood. Fourteen (14) of the fifteen (15) participants properly completed the study and only data for these individuals were used for analysis. HAD scores exceeding 20.0 denote clinical depression, but lower ones can also be associated with dispirited mood. Only two males entered the trial with HAD values exceeding the clinical minimum (21.0 and 23.0). Still, twelve (12) of fourteen (14) subjects showed bettered mood, improved feelings of well being or lessened depression after taking compounds of the invention. Decreases in HAD scores over the two-week timespan were as much as 15 and averaged 5.2. The two clinically depressed subjects showed decreases in HAD values of 5.0 and 15.0. The average HAD score went from 13.5 at the onset of the study to 9.1 after two weeks of taking compounds of the invention, very significant statistically. Participants showed no statistically detectable changes while taking placebo.

After taking compounds of the invention for two weeks, five (5) of fourteen (14) participants had lessened ASEX values, indicating improved sexual response or lessened sexual anxiety, while only two (2) of fourteen (14) males showed the same after two weeks on placebo. Statistical significance was not found for the ASEX changes, but such could be attributed to a small sample size. Sexual benefits of the compounds of the invention were also obviated in the trial through the exit interviews given to all participants. While taking these, a majority of males reported morning erections of the penis greater in size, duration or frequency than usually experienced when not taking the compound. Also, comments by the majority centered about feeling "like a teenager" (direct quote) in terms of energy, sexual and otherwise. It should be noted that personal situations were complicated by unwilling or lacking sex partners. Twelve (12) of fifteen (15) participants also expressed an unsolicited desire to continue using the compounds of the invention. They stated a belief that the compounds of the invention could prove useful to them in a sexual context.

EXAMPLE 3

Compounds of the Invention as an Antidepressant in Human Females

This example further relates to a method for lessening depression and otherwise bettering mood or feelings of well-being, said method comprising the administration to human females of an effective amount of the compounds of the invention, defined above. Compounds of the invention were used to treat eight females with clinical depression, which for three females had been ongoing for at least one year. Participants took the same dose of compounds of the invention as in Example 2, 15-mg each day. A HAD was administered to participants prior to beginning daily doses. Each participant was interviewed every two weeks to check for adverse side effects and for comments on use of the compounds of the invention. A HAD Index was again administered upon completion of the six-week trial.

Referring to Table 3, the results of the study are tabulated.

TABLE 3

HAD summary for clinically-depressed females taking compounds of the invention for six weeks.

| Participant[1] | Initial Value | After Six-Weeks |
|---|---|---|
| 1 | 23.0 | 18.0 |
| 2 | 21.0 | 8.0 |
| 3 | 21.0 | 21.0 |
| 4 | 24.0 | 14.0 |
| 5 | 22.0 | 12.0 |
| 6 | 21.0 | 13.0 |
| 7 | 23.0 | 7.0 |
| 8 | 20.0 | 22.0 |
| Average | 21.9 | 14.4 |

[1]Participants 1-4 initially [Weeks 1-2] were given compounds of invention under guise of its being a vitamin/mineral mixture.
Two-Sample Paired Sign Test - This is one of the stronger or more reliable statistical tests when significance is detected. The question is whether compounds of invention affect depression or feelings of well-being. The Sign-Test is used to statistically ask "how often compounds of invention positively impact depression or feelings of well being". Results are as follows:
HAD, $p < 0.0313$, Significant These data indicate that the compounds of the invention significantly lessen depression. Initial HAD scores exceeded 20 for all subjects. All females were clinically depressed, and their HAD scores averaged 21.9. Six (6) of eight (8) participants showed responses to compounds of the invention in which HAD values decreased 5-16 points, an average decrease of 10.5 over the six-week timespan. The overall average HAD score decreased from 21.9 (clinically depressed) at trial onset to 14.4 (not clinically depressed) after six weeks of use, with two participants ending with HAD values of eight (8) and seven (7). There were only eight females in the trial, but decreases in HAD scores were still statistically significant ($p<0.031$). The antidepressant properties of the compounds of the invention are obviated.

Both excess weight and substance abuse are characterized by either primary or secondary depression. Since such psychological factors affecting excess weight and substance abuse must be treated along with the physiological ones for therapies to be effective in the long term, the compounds of the invention comprise adjunctive treatments for achieving weight loss or reducing the risk of relapse in persons with substance abuse or addiction problems.

EXAMPLE 4

Compounds of the Invention at Concentrations Suitable for Human Therapies from Plants Harvested and Processed in Unique Fashion Example 4 relates to a method for obtaining compounds of the invention at concentrations suitable for human therapies from plants grown to an immature stage of growth. "Concentrations suitable for human therapies" means that compounds of the invention in 10 grams or less of dried plant material make up a daily dose (e.g., 15 mg compounds of the invention as 6-methoxy-2-benzoxazolinone; however, general therapeutically effective daily dosages of compounds of the invention may be between about 5 mcg to about 60 mg). Said dosage may include either the novel compound as it naturally occurs or synthetically, or a combination of both natural and synthetic novel compounds of the present invention.

Specific harvesting and drying conditions are specified herein, as are analytical parameters for determining crop quality. By "specific harvesting and drying conditions", it is meant that compounds of the invention are obtained from plants via circumstances differing from the usual manner in which the plants are handled for the terminal product.

As an example, corn, *Zea mays*, is typically grown to its adult or matured states for its seed-laden cob. At the immature growth stage at which compounds of the invention occur, corn plants have a biomass that portends harvest of a substantial amount of leaf material containing the compounds of the invention at concentrations suitable for human therapies. Hence, dried corn leaves from immature plants become appropriate for the human therapies elucidated herein, or the dried leaves are a resource for the concentration, extraction and purification of the compounds of the invention. There are other monocotyledonous plants with the natural production of compounds of the invention at concentrations suitable for human therapies.

Monocotyledonous flowering plants belong to the plant order of Lilidae (sometimes referred to as a subclass or superorder), which may comprise the following plant families: Alismataceae (water-plantains), Araceae (lords-and-ladies), Butomaceae, Cyperaceae (cotton-grasses, spike-rushes and sedges; sometimes referred to as a plant order), Dioscoreaceae (black bryony), Hydrocharitaceae (waterweeds), Iridaceae (irises), Juncaceae (rushes and woodrushes), Juncaginaceae, Lemnaceae (duck-weeds), Liliaceae (lilies, onions and bluebells), Orchidaceae (orchids), Poaceae (grasses—also named Graminae), Potamogetonaceae (pondweeds), Sparganiaceae (bur-reeds), Typhaceae (bulrushes), and Zosteraceae. It is contemplated that compounds of the invention may be derived, isolated, harvested and/or extracted from monocotyledonous plants selected from any of the above identified plant families and/or orders. Preferred embodiments of compounds of the invention may be selected from the families of Cyperaceae and Poaceae (also referred to as Graminae). These families include the cereal grasses (e.g., corn, wheat, barley, oats, rice and rye) and the hay and pasture plants (e.g., sorghum, sugarcane, timothy, bent grass, bluegrass, orchard grass, and fescue). These families may also include wild grasses, millet, bamboo, Job's Tears (*Coix lachryma-jobi; Coix aquatica*) and other barley-like grasses.

Monocotyledonous plants as sources of compounds from preferred embodiments of the invention may be selected from the group consisting of corn, wheat, barley, rye, oats, rice, sorghum, millet, bamboo, Job's Tears, barley-like grasses, and wild grasses, by growing the plant to an immature life history stage (i.e., before plant maturity) and harvesting the plant. The example of corn, *Zea mays*, is not intended to be limiting to the scope of the source of compounds of the invention. In all cases, harvest and processing needs to be done in a novel and unique fashion relative to the usual manner in which the plants are handled, and the analytical parameters for indirectly determining crop quality with respect to the compounds of the invention, described below, are applicable.

Growing corn to obtain the compounds of the invention is initially done in a conventional fashion, but seeds are planted more densely than is the case for conventional crops because of the smaller size of plants at harvest. Harvest time is done while plants are immature. For corn, this immature plant harvesting may happen when plants are no more than about thirty (30) to about forty-five (45) centimeters tall, about five weeks after planting. Preferably, embodiments of the invention may also utilize harvesting immature corn plants that are between about forty-five (45) centimeters to about 122 centimeters in height, and between about five weeks to about eight weeks after planting are sought and preferably less than ten weeks. As a general reference, mature corn plants are typically more than 180 centimeters in height and are grown for about four (4) to about five (5) months after planting. For corn, harvesting is preferably done by cutting plants at 3-4 centimeters above the ground. Severed plants may be gathered and may be dried at temperatures held at about 40° Celsius (C.) to about 45° C. Empirical studies showed that this temperature range helps maximize conversion of the precursors of compounds of the invention to the active molecules.

In a trial plot in southern Illinois, approximately 38,000 corn plants yielded 137 kilograms (300 pounds) of dried (96% dry weight) corn leaves with suitable levels of compounds of the invention. Analyses via mass spectroscopy showed that substantive amounts of the compounds of the invention were in dried corn leaves after five (5) weeks of growing time. Five (5) random samples of dried corn leaves were obtained for analysis. For each dried corn leaf sample, a one-gram portion was homogenized in 10-ml distilled water, incubated at 25° C. for one (1) hour, boiled for thirty (30) min, and then centrifuged for ten (10) min at 3600 rpm. The resulting supernatant was extracted three (3) times with ten (10) ml reagent-grade dichloromethane per extraction. The three (3) extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using 0.06-, 0.60- and 1.20-.mu.g injections of pure, synthetic 6-MBOA (Sigma, Saint Louis, Mo.) in methanol solution and was reproducible at a five percent (5%) level.

6-MBOA occurred in dried corn leaves at levels suitable for human consumption. Samples averaged ten (10) mg/g 6-MBOA, with individual samples assaying as follows: eight (8), nine (9), ten (10), ten (10), and twelve (12) mg/g 6-MBOA, respectively. At such concentrations, less than two (2) grams dried corn leaves are needed to make up a daily human dose. This makes corn leaves, as uniquely grown, harvested and dried herein, a suitable source of compounds of the invention. For comparison purposes, leaves from plants grown more than eight (8) weeks were analyzed for 6-MBOA. Virtually none was present.

Previous work by the inventors indicated that higher levels of the compounds of the invention are associated with multiple biochemical parameters that indicate crop quality or adequacy with respect to the compounds of the invention. In those plants containing compounds of the invention at concentrations suitable for human use total phenols are at concentrations greater than 17.0 mg/gm (dry weight) but combined amounts of 4-hydroxycinnamic acid and 4-hydroxy-3-methoxycinnamic acid total no more than 1.5 mg/gm (dry weight), as determined through chromatography. For invention, the above mentioned parameters for total phenols and combined amounts of 4-hydroxycinnamic acid and 4-hydroxy-3-methoxycinnamic acid are instituted here as elements of the invention as it pertains to plants. For the corn leaf samples of Example 2, total phenols averaged 19.1 mg/gm and the cumulative total for cinnamic acids averaged 0.9 mg/gm.

EXAMPLE 5

Compounds of the Invention from Parts of Animals

The main food of deer and elk (Cervidae) for most of the year is browse, the growing tips of low-growing, woody plants. However, casting of hard antlers from the previous year coincides with a spring flush in natural pasturage and an accompanying shift to a diet of grasses, chiefly sprouting and immature ones. Such grasses are at developmental stages in which 6-MBOA and related compounds are most prevalent.

After casting, new antlers begin their development. These growing antlers are nourished by blood vessels from a covering of skin, called velvet. An antler grows from the tip with tissue laid down as the tip advances. A velvet antler tip has a soft cartilaginous internal structure and high fat content, contrasting the rest of the antler with its ossified cartilage and little fat.

Air-dried and freeze-dried velvet antler samples were obtained. These came from commercially farmed Canadian Wapiti and New Zealand red deer, both subspecies of elk, *Cervus elaphus*. All animals had been maintained on grassy pasturage. The samples were from velvet antlers that had been growing fifty-five (55) to sixty-five (65) days, and included both tips, defined as the region five (5) cm or less in length starting at the apex, as well as other, more matured parts of the antler.

For each sample of dried antler, a one-gram portion was homogenized in ten (10)-ml distilled water, incubated at 25° C. for one (1) hour, boiled for thirty (30) min, and then centrifuged for ten (10) min at 3600 rpm. The resulting supernatant was extracted three (3) times with ten (10) ml reagent-grade dichloromethane per extraction. The three (3) extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using, 0.06-, 0.60- and 1.20-mcg injections of pure, synthetic 6-MBOA (Sigma, Saint Louis, Mo.) in methanol solution and was reproducible at a five percent (5%) level.

Referring to Table 4, the observations of Example 5 may be summarized as follows:

TABLE 4

6-MBOA in Dried Velvet Antler from Elk, *Cervus elaphus*.

| Animal | Origin | Tip or Other | Drying Method | 6-MBOA (mg/g dry weight) |
|---|---|---|---|---|
| Wapiti | Canada | Tip | Air | 2.5 |
| Wapiti | Canada | Tip | Air | 2.8 |
| Wapiti | Canada | Other | Air | 0.3 |
| Red Deer | New Zealand | Tip | Freeze | 1.9 |
| Red Deer | New Zealand | Other | Freeze | 0.5 |

These data indicate 6-MBOA was present in all tip samples, with little or none present in those from the more matured parts of the antler. Notably, amounts of 6-MBOA from velvet antler tips exceeded those typically found in grasses less than a week after sprouting, the stage of growth with the most 6-MBOA. These results show that ingested 6-MBOA is accumulated or concentrated in velvet antler tips, and as such represent a means for obtaining the compounds of the invention in concentrations suitable for human use.

Many animals eat grasses and other monocotyledonous plants. Such animals may also be accumulating compounds of the invention in body parts, most likely in those characterized by high fat contents. Obtaining compounds of the invention from body parts other than the antlers of elk and deer and from animals other than elk or deer are not precluded from invention.

EXAMPLE 6

Compounds of the Invention for Weight Loss

Recruitment of Participants

Overweight human females and males were preferentially recruited for this look at weight loss properties of the compounds of the invention. For reasons of safety, precluded from participation were individuals with moderate or worse hypertension (Systolic>160, Diastolic>100); Class 2 or Morbid Obesity (Body Mass Index>35, see below); and/or health problems of a debilitating, life-threatening or otherwise serious nature (multiple sclerosis, emphysema, diabetes, etc.). Twenty-four (24) individuals had been initially screened, while fourteen (14) females and six (6) males ultimately took part in the study. Ages of the twenty (20) participants ranged from thirty-one (31) to fifty-four (54) years, and averaged thirty-eight (38) years.

Test and Control Groups

The twenty (20) participants were randomly assigned to Test and Control Groups, with ten (10) participants in each group. In particular, those participants in the "Test Group" were given the novel compounds of the present invention which were produced and delivered in gelatin capsules (e.g., Size 00). The novel compounds of the invention were obtained from appropriately chosen, grown, dried and ground leaves from the corn plant (*Zea mays*), further to the methods of harvesting as described hereinabove. In one presently preferred embodiment, the dosage was standardized to 6-MBOA content, for which daily cumulative dose was ninety (90) micrograms for each participant. Although it will be appreciated that compounds having the general chemical structure as set forth in formulae I, II, III, and generally as IV, 6-MBOA was used in the present exemplary study. It will be appreciated, therefore, that other novel compounds of the present invention, consistent with the general chemical structure as set forth in formulae I, II, III, and IV are within the spirit and scope of the present invention.

Moreover, the novel compounds of the present invention may be derived, isolated, and/or extracted from monocotyledonous flowering plants belong to the plant order of Lilidae, consistent with the harvesting methods described hereinabove or by means of chemical synthesis. It is further contemplated that the novel compounds of the invention may be obtained by a combination of harvesting from natural sources, as described hereinabove, and by chemical synthesis. Delivery of a dosage of the novel compounds of the present invention may include either the novel compound as it naturally occurs or synthetically, or a combination of both natural and synthetic.

Those participants in the "Control Group" were given ground, dried parsley leaves (*Petroselinum hortense*) delivered in gelatin capsules (e.g., Size 00). This placebo preparation comprising parsley visually resembled capsules containing the compounds of the invention, but was instead made from a plant well recognized as having no effects on weight loss or other aspects of weight control; on mood, depression or feelings of well being; and/or on sexual function, arousal, or performance.

Study Design

Participants were subjected to the same administration schedules without-knowledge as to whether they belonged to the Test Group or the Control Group. All were instructed to take two (2) capsules at 0.5-1.0 hour before meals, three (3) times per day, for thirty (30) successive days. Participants were told that they were receiving a dietary supplement that might better mood and otherwise improve disposition or outlook, but were not instructed that the formulation might affect weight or effect weight loss. Furthermore, "overweight" had been a long-term condition for virtually all participants. Because of these pre-existing eating behaviors and the fact that participants were blinded to the knowledge that involvement in the study might lead to weight loss, independent assignment of participants to either the Test Group or Control Group was not believed to significantly effect eating behaviors and associated weight consequences.

Visits and Measurements

At the beginning of the study, participants in both the Test Group and the Control Group were given the self administered Goldberg Depression Scale to maintain the illusion of a mood-related study. All participants also had their blood pressures taken and were weighed (done before breakfast while nude or in underwear; measured on a calibrated electronic scale to the nearest 0.1 kilograms) prior being given the novel compounds of the present invention or placebo, respectively. All participants were also weighed at the end of the study (e.g., thirty (30) days). The height of each participant, while barefoot or wearing socks, was determined only at the onset of the study, whereas Body Mass Index (BMI) values were calculated both at the onset and at the end of the study. As known in the art, BMI is a measure of body fat, and thus weight-related health risks, based on height and weight that applies to both adult men and women. BMI is generally calculated as follows:

BMI equals a person's weight in kilograms divided by height in meters squared; or $$BMI = \frac{\text{Weight in Kilograms}}{(\text{Height in Meters}) \times (\text{Height in Meters})} = kg/m2$$

A BMI over thirty (30) is typically considered obese; a BMI between twenty-five (25) and 29.9 is typically considered overweight; and a BMI between 18.5 and 24.9 is typically considered healthy. Older people tend to have more body fat than younger adults with the same BMI, and some clinicians consider BMI values under twenty-seven (27) to be normal and healthy for individuals over forty (40) years old.

Statistical Analysis

With only ten (10) participants in each Group, assuming normal distributions for the data was inappropriate. In order to compensate for a potentially non-normal distribution of study data, a non-parametric test was utilized for statistical analysis. As known in the art, the Wilcoxon-Mann-Whitney U Test (sometimes referred to as the Wilcoxon Rank Sum Test) is one of the more powerful of non-parametric tests for comparing data distributions in two populations (e.g., Test Group and Control Group).

Results

Referring to Table 5, the weight and BMI for each of the study participants is illustrated showing the pre-treatment and post-treatment results following thirty (30) days of oral administration of the 6-MBOA compound of the present invention, or alternatively, a placebo.

TABLE 5

Weight and Body Mass Indices before and after a 30-day administration of compounds of the invention or a control.

| | | | Weight (kg) | | | Body Mass Index (BMI)[1] | | |
|---|---|---|---|---|---|---|---|---|
| | Sex | Height (cm) | Beginning | 30 Days | Difference | Beginning | 30 Days | Difference |
| Test Group | F | 165 | 74.9 | 73.5 | −1.4 | 27.5 | 27.0 | −0.5 |
| | F | 175 | 81.7 | 83.0 | +1.3 | 26.6 | 27.1 | +0.5 |
| | F | 173 | 89.0 | 87.5 | −1.5 | 29.8 | 29.2 | −0.6 |
| | F | 173 | 91.3 | 88.7 | −2.6 | 30.6 | 29.6 | −1.0 |
| | F | 175 | 79.9 | 78.8 | −1.1 | 26.0 | 25.7 | −0.3 |
| | F | 175 | 81.3 | 78.4 | −2.9 | 26.4 | 25.6 | −0.8 |
| | F | 168 | 84.0 | 82.6 | −1.4 | 29.9 | 29.3 | −0.6 |
| | M | 178 | 78.5 | 78.8 | +0.3 | 24.8 | 24.9 | +0.; |
| | M | 175 | 85.8 | 86.7 | +0.9 | 27.9 | 28.3 | +0.4 |

TABLE 5-continued

Weight and Body Mass Indices before and after a 30-day administration of compounds of the invention or a control.

|  | Sex | Height (cm) | Weight (kg) | | | Body Mass Index (BMI)[1] | | |
|---|---|---|---|---|---|---|---|---|
|  |  |  | Beginning | 30 Days | Difference | Beginning | 30 Days | Difference |
|  | M | 178 | 89.9 | 88.4 | −1.5 | 28.4 | 27.9 | −0.5 |
| Avg |  | 173.5 | 83.6 | 82.6 | −0.9 | 27.8 | 27.5 | −0.3 |
| Control Group | F | 178 | 80.4 | 80.0 | −0.4 | 25.4 | 25.2 | −0.2 |
|  | F | 163 | 82.2 | 82.8 | +0.6 | 31.1 | 31.2 | +0.1 |
|  | F | 173 | 89.4 | 88.0 | −1.4 | 30.0 | 29.4 | −0.6 |
|  | F | 178 | 89.9 | 90.3 | +0.4 | 28.4 | 28.5 | +0.1 |
|  | F | 175 | 87.2 | 87.6 | +0.4 | 28.4 | 28.6 | +0.2 |
|  | F | 173 | 79.0 | 77.7 | −1.3 | 26.5 | 26.0 | −0.5 |
|  | F | 170 | 83.5 | 83.0 | −0.5 | 28.8 | 28.7 | −0.1 |
|  | M | 180 | 90.8 | 91.5 | +0.7 | 28.0 | 28.2 | +0.2 |
|  | M | 183 | 99.9 | 99.4 | −0.5 | 29.8 | 29.7 | −0.1 |
|  | M | 185 | 94.9 | 95.7 | +0.8 | 27.6 | 28.0 | +0.4 |
| Avg |  | 175.8 | 87.7 | 87.6 | −0.1 | 28.4 | 28.4 | −0.1 |

[1]BMI = weight in kilograms/(height in meters)$^2$ = kg/m$^2$
F = female;
M = male;
cm = centimeters;
kg = kilograms;
Avg. = average.

The test group was given compounds of the invention packaged in gelatin capsules. The dosage was standardized to 6-MBOA content for which the total daily dose was 90 micrograms (μg). The control group took ground, dried parsley leaves in gelatin capsules. The Wilcoxon-Mann-Whitney U Test was used to assess differences between the test and control groups. With 20 participants equally divided into two groups, homogeneity of variance and normal distributions, data attributes required by most parametric statistics, could not be assumed. Thus, a nonparametric test, the Mann-Whitney U Test, was used to compare the equivalency of changes in the Test and Control Groups. For the Wilcoxon-Mann-Whitney U Test, the value calculated for determining significance is called the "U" statistic.

Primary interests centered about changes in absolute body weight after talking the 6-MBOA compound of the invention for thirty (30) days. Both the participants in Test Group and the Control Group showed weight loss and BMI decreases, but magnitudes of the weight loss differed. For "Weight", the Test Group showed a nine-fold greater loss than did the Control Group, or almost about one (1) kilogram on average in the Test Group contrasting to about 0.1 kilograms in the Control Group. BMI values also decreased three-fold more for the Test Group, in comparison to the Control Group.

On a case-by-case basis, differences between participants in the Test and Control Groups were even more striking. Seven (7) of the ten (10) participants in the Test Group experienced losses ranging from about 1.1 to about 2.9 kilograms, and averaging about 1.8 kilograms. In the Control Group, some of the participants (five (5) of the ten (10)) lost weight. However, the amount of weight lost in the Control Group was substantively less than in the weight loss of the participants in the Test Group. The weight lost in the Control Group ranging from about 0.4 to about 1.3 kilograms and averaging only about 0.8 kilograms.

With the Wilcoxon-Mann-Whitney U Test, the null hypothesis was that medians did not differ between the participants in the Test and Control Groups. In "Difference" for "Weight", the Test Group median differed significantly from the Control one (U=27.0; P=0.04). On average, more weight was lost by Test Group participants than by Control Group participants. Differences between the Test and Control Groups for "Weight" at the "Beginning" were not significant (U=32.5; P=0.10), meaning that baseline weights in the Test and Control Groups may have been similar. On the other hand, "Weight" at the "End" did significantly differ (U=98.5; P=0.05). The results therefore support a finding that weight reduction is better associated with having taking the novel compounds of the present invention for a period of about one month.

BMI comparisons did not reveal statistical differences, but this was largely due to the small sample size. The statistical problem with smaller sample size may be appreciated for example, and not by way of limitation, by looking at differences in "End" values for the Test Group versus the Control Group. These "End" values between the groups were not great enough to show as significantly different (U=34.0; P=0.12). Results for "Difference" between the Test Group and Control Group (U=31.5; P=0.08) were also not significant. However, the mean value for "Difference" decreased three-fold more in the Test Group (−0.3) than in the Control Group (−0.1). This disparity in the mean values for "Difference" is further evidence that the novel compounds (e.g., 6-MBOA) of the present invention may contain weight loss properties. With a greater number of participants (i.e., greater study size sample), significant results between the Test and Control Groups comparisons and even more profound demonstration of weight reduction from using the novel compounds of the present invention are considered to be highly likely.

Discussion and Conclusions

As disclosed herein, novel compounds of the present invention positively affect mood. It was therefore hypothesized by the inventors that the novel compounds of the present invention may have weight loss properties. This example or study is consistent with the initial hypothesis and premise.

Weight loss by the Control Group participants (significantly less than the Test Group), may be attributed to the placebo effect. The placebo effect is a psychological phenomenon, due to belief in a treatment or to a subjective feeling of improvement. According to the placebo effect it was believed plausible that participants in the Control Group might have some weight loss due to their expectation that they might be receiving an agent which could improve mood. It is possible that the expectation of an improved mood, regardless of reason, could result in a reduced caloric intake, and subsequently result in weight loss. Even with the possible placebo effect, the significant nine-fold greater weight loss in the Test Group versus the Control Group is supportive that the novel compounds of the present invention are an effective weight loss treatment or regimen.

Given the weight loss demonstrated herein, both beta-adrenergic agonistic and alpha-adrenergic antagonistic receptor effects are considered consequences of using the novel compounds of the present invention. As earlier stated, the novel compounds of the present invention have been shown to be beta-adrenergic agonists. In regard to fat cells, beta-adrenergic agonist activity is considered fundamental for releasing lipids and thus achieving lipolysis or fat loss. Not only did the compounds of the present invention effect mobilization of fatty acids or lipids from fat cells, but these compounds did this without harsh side effects, such as the jitters and hypertension associated with ephedrine-based products. The weight loss realized by participants in the Test Group also indicates alpha-adrenergic (e.g., alpha 2-adrenergic) antagonist activity with the novel compounds of the present invention, given that such activity facilitates mobilization from fat cells of lipids that otherwise might not be released very easily. Alpha-adrenergic antagonists like the novel compounds comprising the present invention are particularly desirable for purposes of reducing those areas of fat storage considered more difficult to trim, like the obliques in men and lower body in women.

In consort with their weight loss properties, the novel compounds of the present invention also act as appetite suppressants, sometimes referred to as appetite depressants. As known in the art, appetite suppressants are generally referred to as agents for decreasing appetite such that caloric intake and perhaps ingestion of certain foods are reduced. These properties of the novel compounds of the present invention may be demonstrated by the effect on food consumed, both by type of food and caloric intake, by those participants who were administered the novel compounds of the present invention.

Interviews with the participants revealed that, prior to the onset of the study, caloric intake by certain overweight female participants, (four (4) of the seven (7) Test Group women—the lesser overweight participants (BMI average 26.6)), was 2,100 kilocalories (kcal) per day on average. The average value for women of normal body weight is 1,900 kcal per day. This is a difference of only ten percent (10%) and may have included such factors as poor diet selections and physical inactivity in the overweight female participants.

Women of normal body weight tend to eat whole grains, fruits, vegetables, low-fat protein sources and foods otherwise considered to be of a healthful and nutritious nature. Items high in carbohydrates and fats, along with low quantities of fiber and protein figured prominently in the diets of the overweight women in the study. For example, one female participant had a propensity to eat an abundance of bread or pastries in lieu of or along with other foods, while another female participant routinely skipped breakfast but also snacked on chocolate candy bars and sugar-fortified carbonated beverages.

The three (3) remaining participants had been routinely eating even more at the onset of the study, with their initial caloric consumption ranging from about 2,400 kcal to about 3,000 kcal per day, with about 2,700 kcal on average. These participants had a mean BMI of 30.1 and were generally more overweight than the other four (4) Test Group females (BMI average 26.6). Although the three (3) remaining female participants consumed about 600 kcal per day more than did the other females participants in the Test Group, all female participants were uniform in that foods of lesser nutritional quality made up prominent portions of their diets.

After administering the compounds of the invention for thirty (30) days, the average caloric intake for the four (4) females with lesser BMI (average 26.6) had decreased by more than 100 kcal per day. These participants also reported lessened cravings for certain food items. For example, the female participant who skipped breakfast and consumed chocolate candy bars and sugar-fortified carbonated beverages experienced decreased desire for these food items and decreased her body weight by 2.9 kilograms. In addition, the female participant who ate a higher proportion of bread and pastries decreased her intake of such items and decreased her body weight by 1.4 kilograms.

Similar results and observations were seen in the overweight females with an average BMI of 30.1 when the study began. They also experienced reduced caloric intakes while receiving compounds of the invention, and decreased body weight, on average, by about 1.8 kilograms. Moreover, these three (3) female participants reported their desire to eat had abated by the end of the thirty (30) day test period. The data and observations of the study illustrate significant activity of the compounds of the present invention in reducing a desire to consume sugars, simple carbohydrates (e.g., snack foods) and unhealthy saturated fats (e.g., snack foods and meats). In this group of overweight female participants, average daily food intake was reduced by about 230 kcal following the thirty (30) days administration of the compounds of the present invention. It has been found, therefore, that compounds of the present invention are responsible for suppression or depression of appetite in the participants in the Test Group.

Given that the novel compounds of the present invention have both weight loss and mood bettering properties, such properties may prove to be a beneficial therapy for arthritis. It is well known in the art, that osteoarthritis is a degenerative joint disease and the most common form of arthritis. Unlike joint problems caused by swelling or inflammation, osteoarthritis stems primarily from a breakdown of the connective tissues that bind muscles and bones together. The ensuing damage includes deterioration of joint surfaces, which no longer mesh smoothly and instead cause considerable pain. Joint problems are usually worsened by excessive weight. For example, the knees bear a considerable load even during such simple activities as walking, whereas any decrease in overall body weight can positively affect the performance or quality of life in arthritic individuals. Meanwhile, preparations that improve mood have been found to ameliorate the debilitating pain associated with arthritis or otherwise better tolerance of arthritic conditions.

Likewise, the novel compounds of the present invention may be advantageous to diabetic and hyperglycemic people, for whom weight loss and mood enhancing medications can improve glycemic control. The compounds of the present invention also provide applicable therapy for other disorders. For example, weight loss may improve physical functioning in fibromyalgia patients, while mood-enhancing medications may alleviate other adverse symptoms of this condition. Weight loss may also help eliminate or otherwise diminish sleep apnea, making the novel compounds of the present invention valuable for treatment of this condition.

EXAMPLE 7

Alternative Embodiments of the Novel Compounds

Any number of alternative embodiments of precursors of phenolic compounds of the present invention may be contemplated as falling within the spirt and scope of the present invention. In particular, Formula V, below, is a general chemical formula depicting a generic representation of alternative embodiments of precursors of phenolic compounds of the present invention.

Formula V - A compound according to the formula:

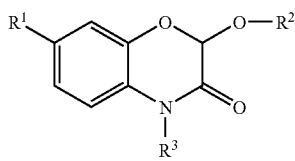

Wherein "$R^1$" is selected from the group consisting of H and $OCH_3$;

Wherein "$R^2$" is selected from the group consisting of H and Glucose (as a glucoside)

Wherein "$R^3$" is selected from the group consisting of H, OH, and $OCH_3$;

or pharmaceutically acceptable salts thereof.

As shown, such embodiments of novel compounds of the present invention may include benzoxazinoids-cyclic hydroxyamic acids, lactams, and corresponding glucosides. As contemplated herein, substitution at the "$R^1$" position may be accomplished with a member selected from the group consisting of H and $OCH_3$. Substitution at the "$R^2$" position may be accomplished with a member selected from the group consisting of H and glucose (as a glucoside). Substitution at the "$R^3$" position may be accomplished with a member selected from the group consisting of H, OH, and $OCH_3$.

Referring now to Compounds 8-17, below, a series of chemical formulae, according to the generic representation shown in Formula V, illustrate chemical structures for representative compounds of further embodiments of novel compounds of the present invention.

8. 2,4-dihydroxy-1,4-benzoxazin-3-one (DIBOA)

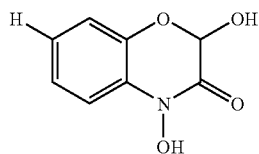

9. 2,4-dihydroxy-1,4-benzoxazin-3-one-glucoside (DIBOA-Glc)

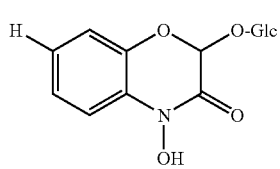

10. 2,4-dihydroxy-7-methoxy-1,4-benzoxazin-3-one (DIMBOA)

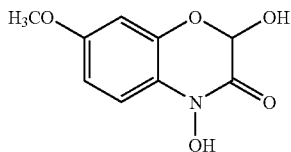

11. 2,4-dihydroxy-7-methoxy-1,4-benzoxazin-3-one-glucoside (DIMBOA-Glc)

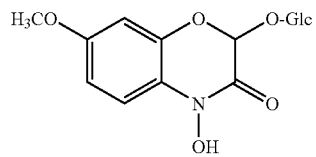

12. 2-hydroxy-1,4-benzoxazin-3-one (HBOA)

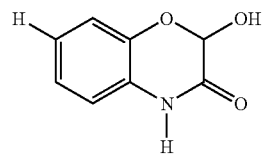

13. 2-hydroxy-1,4-benzoxazin-3-one-glucoside (HBOA-Glc)

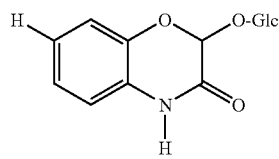

14. 2-hydroxy-7-methoxy-1,4-benzoxazin-3-one (HMBOA)

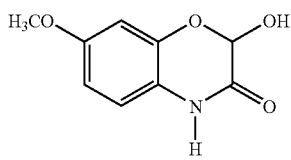

15. 2-hydroxy-7-methoxy-1,4-benzoxazin-3-one-glucoside (HMBOA-Glc)

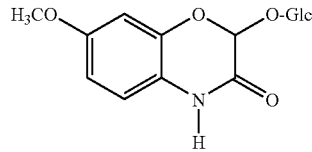

16. 2-hydroxy-4,7-dimethoxy-1,4-benzoxazin-3-one (HDMBOA)

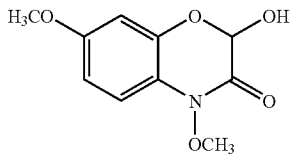

17. 2-hydroxy-4,7-dimethoxy-1,4-benzoxazin-3-one-glucoside (HDMBOA-Glc)

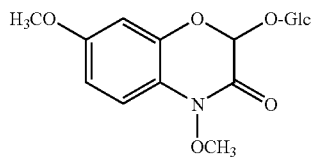

Specifically, compound 8 illustrates a chemical formula for 2,4-dihydroxy-1,4-benzoxazin-3-one (DIBOA). DIBOA may also have a glucose molecule to form a glucoside (also referred to as a glycoside), DIBOA-Glc, which is shown as compound 9. As illustrated, compound 10 depicts a chemical formula for 2,4-dihydroxy-7-methoxy-1,4-benzoxazin-3-one (DIMBOA). DIMBOA may also exist in combination with glucose molecule to form a glycoside compound (DIMBOA-Glc), which is shown compound 11. Compound 12 illustrates a chemical formula for 2-hydroxy-1,4-benzoxazin-3-one (HBOA). A glycoside may also form between HBOA and a glucose molecule (HBOA-Glc) and is shown compound 13. Compound 14 depicts a chemical formula for 2-hydroxy-7-methoxy-1,4-benzoxazin-3-one (HMBOA). HMBOA may also contain a glucose molecule to form HMBOA-Glc, which is depicted compound 15. Additionally, compound 16 illustrates a chemical formula for 2-hydroxy-4,7-dimethoxy-1,4-benzoxazin-3-one (HDMBOA). Wherein, compound 17 illustrates a glucoside formed between HDMBOA and glucose (HDMBOA-Glc).

In the foregoing examples, glucose molecules may be bonded to a respective aglycone (i.e., non-sugar) compound (e.g., DIBOA, DIMBOA, HBOA, HDMBOA, 6-MBOA) to form a glycoside. As appreciated, glucose molecules typically are in the form of a pyranose (i.e., cyclic 6-carbon ring), which may be referred to as a glucopyranose. Glucopyranose compounds usually bond with the aglycone portion as an hemiacetal. Configurations of glycoside compounds in yet other presently preferred embodiments of the present invention may be found in the (2R)-configuration. It is intended, however, that other forms of glucose and configurations of glycosides are contemplated to be within the spirt and scope of the novel compounds of the present invention. It is intended, therefore, that the presently preferred embodiments of novel compounds of the present invention, as shown in Example 7, be viewed as exemplary of the principles of the present invention, and not as restrictive to any particular formula, structure, or method for implementing and/or practicing the present invention.

Since the novel compositions of phenolic compounds and precursors of phenolic compounds of the present invention are configured to promote weight loss, suppress appetite, and enhance mood, it will be readily appreciated that a method for promoting weight loss, suppressing appetite and for enhancing mood includes phenolic compounds belonging to related chemical families of which 6-methoxy-2,3-benzoxazolinone (6-MBOA) is a member as described hereinabove. It is intended, therefore, that the examples provided herein be viewed as exemplary of the principles of the present invention, and not as restrictive to a particular structure or method for implementing those principles.

It will be further appreciated that the novel compositions of phenolic compounds and precursors of phenolic compounds belonging to related chemical families as defined herein of which 6-methoxy-2,3-benzoxazolinone (6-MBOA) is a member, may be administered in any manner known to those ordinary skill in the art, including but not limited to, oral, parenteral, sublingual, topical, transdermal, intramuscular, or inhalation, and may also contain excipients chosen in accordance with the dosage form adopted. Moreover, the dosage of the extract compositions given to an individual may vary on the basis of several considerations without departing from the spirit and scope of the present invention and will, accordingly, depend on the targeted individual's particular case to be treated.

From the above discussion, it will be appreciated that the present invention provides methods of promoting weight loss, suppressing appetite or enhancing mood using phenolic compounds and precursors of phenolic compounds belonging to related chemical families of which 6-methoxy-2,3-benzoxazolinone (6-MBOA) is a member. While specific dose levels are used in the Examples, these are merely examples and effective dose levels may vary to a large extent, and preferred dose levels may vary with the conditions being treated and the size or sex of the person being treated. Dose levels do not appear to be critical as long as an effective amount is given.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow. All changes which come within the meaning and range of equivalency of the claims are to be embraced within their scope.

What is claimed and desired to be secured by United States Letters Patent is:

1. A process for promoting weight loss and/or suppressing appetite and/or enhancing mood and/or treating at least one of fibromyalgia, sleep disorder, hyperglycemia, arthritis, or substance addiction in a human by the administration of an amount of a composition defined as:

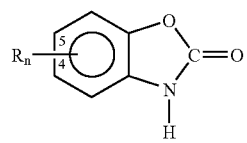

wherein "R" represents $C_1$-$C_4$ alkoxy, with stipulation that R is in the 4 or 5 ring position;
wherein "n" represents one of the integers 0, 1 or 2;
or a pharmaceutically acceptable salt thereof,
    said amount of said composition comprising a daily dosage of between about 5 mcg and about 60 mg to promote weight loss and/or suppress appetite and/or enhance mood and/or treat at least one of fibromyalgia, sleep disorder, hyperglycemia, arthritis, or substance addiction in a human, wherein said composition is obtained from at least one of (i) a leafy and/or immature plant part of one or more monocotyledonous plants, (ii) animal tissue or (iii) chemical synthesis.

2. A process as defined in claim 1, wherein said composition comprises 6-methoxy-2,3-benzoxazolinone defined as:

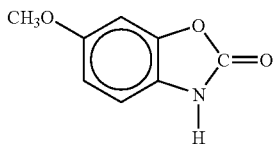

or a pharmaceutically acceptable salt thereof,
wherein said 6-methoxy-2,3-benzoxazolinone is obtained from a leafy and/or immature plant part of one or more monocotyledonous plants.

3. A process as defined in claim 1, wherein said amount of said composition comprises a daily dosage of about 5 mg.

4. A process as defined in claim 1, wherein said composition is obtained at least in part from a leafy and/or immature plant part of one or more monocotyledonous plants selected from the group consisting of corn, wheat, barley, rye, oats, rice, sorghum, millet, bamboo, Job's Tears, barley-like grasses, and wild grasses.

5. A process as defined in claim 4, wherein said leafy and/or immature plant part is dried.

6. A process as defined in claim 5, wherein said leafy and/or immature plant part is dried at a temperature in the range of between about 40° C. and about 45° C.

7. A process as defined in claim 5, wherein said leafy and/or immature plant part contains phenols in total amounts greater than 17.0 mg/gm (dry weight).

8. A process as defined in claim 5, wherein said leafy and/or immature plant part contains combined amounts of 4-hydroxycinnamic acid and 4-hydroxy-3-methoxycinnamic acid totaling no more than 1.5 mg/gm (dry weight).

9. A process as defined in claim 4, wherein said leafy and/or immature plant part is obtained from an immature corn plant, *Zea mays*.

10. A process as defined in claim 9, wherein said immature corn plant has been grown to a height between about 45 centimeters and about 122 centimeters.

11. A process as defined in claim 9, wherein said immature corn plant has been grown to a height that does not exceed between about 30 centimeters and about 45 centimeters.

12. A process as defined in claim 9, wherein said immature corn plant has been grown for less than ten weeks after planting.

13. A process as defined in claim 1, wherein said composition is administered in a manner selected from the group consisting of: (1) oral administration; (2) intranasal administration; (3) transmucosal administration; (4) parenteral injection; (5) implant for sustained release; and (6) transdermal patch.

14. A process for promoting weight loss and/or suppressing appetite in a mammal by the administration of an amount of a composition defined as:

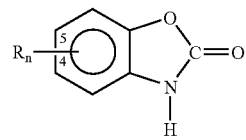

wherein "R" represents $C_1$-$C_4$ alkoxy, with stipulation that R is in the 4 or 5 ring position;
wherein "n" represents one of the integers 0, 1 or 2;
or a pharmaceutically acceptable salts thereof;
said amount of said composition comprising a daily dosage of between about 5 mcg and about 60 mg to promote weight loss and/or suppress appetite in a mammal; and
wherein said composition is obtained at least in part from a leafy and/or immature plant part of one or more monocotyledonous plants selected from the group consisting of corn, wheat, barley, rye, oats, rice, sorghum, millet, bamboo, Job's Tears, barley-like grasses, and wild grasses.

15. The process as defined in claim 14, wherein said composition comprises 6-methoxy-2,3-benzoxazolinone defined as:

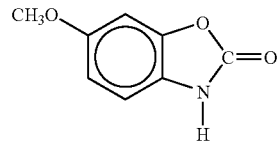

or a pharmaceutically acceptable salt thereof.

16. The process as defined in claim 14, wherein said amount of said composition comprises a daily dosage of about 15 mg.

17. The process as defined in claim 14, wherein said leafy and/or immature plant part is dried.

18. The process as defined in claim 17, wherein said leafy and/or immature plant part is dried at a temperature in the range of between about 40° C. and about 45° C.

19. The process as defined in claim 17, wherein said leafy and/or immature plant part contains phenols in total amounts greater than 17.0 mg/gm (dry weight).

20. The process as defined in claim 17, wherein said leafy and/or immature plant part contains combined amounts of 4-hydroxycinnamic acid and 4-hydroxy-3-methoxycinnamic acid totaling no more than 1.5 mg/gm (dry weight).

21. The process as defined in claim 14, wherein said leafy and/or immature plant part is obtained from an immature corn plant, *Zea mays*.

22. The process as defined in claim 21, wherein said immature corn plant has been grown to a height between about 45 centimeters and about 122 centimeters.

23. The process as defined in claim 21, wherein said immature corn plant has been grown to a height that does not exceed between about 30 centimeters and about 45 centimeters.

24. The process as defined in claim 21, wherein said immature corn plant has been grown for less than ten weeks after planting.

25. The process as defined in claim 14, wherein said amount of said composition is administered in a manner selected from the group consisting of: (1) oral administration; (2) intranasal administration; (3) transmucosal administration; (4) parenteral injection; (5) implant for sustained release; and (6) transdermal patch.

26. A process as defined in claim 14, wherein a portion of said composition is obtained by at least one of chemical synthesis or isolation, extraction and/or purification from a natural plant or animal source.

27. A process as defined in claim 14, wherein a portion of said composition is obtained from the leafy and/or immature plant part of one or more monocotyledonous plants and standardized with a synthesized form of said composition.

28. A process as defined in claim 14, said composition being administered to a human, said amount of said composition further enhancing mood and/or treating at least one of fibromyalgia, sleep disorder, hyperglycemia, arthritis, physical or psychological condition caused by stress, or substance addiction in said human.

29. A process for promoting weight loss and/or suppressing appetite and/or enhancing mood and/or treating at least one of fibromyalgia, sleep disorder, hyperglycemia, arthritis, physical or psychological condition caused by stress, or substance addiction in a human by the administration of an amount of a composition defined as:

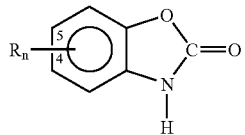

wherein "R" represents $C_1$-$C_4$ alkoxy, with stipulation that R is in the 4 or 5 ring position;

wherein "n" represents one of the integers 0, 1 or 2;

or a pharmaceutically acceptable salt thereof;

said amount of said composition comprising a daily dosage of between about 5 mcg and about 60 mg to promote weight loss and/or suppress appetite and/or enhance mood and/or treat at least one of fibromyalgia, sleep disorder, hyperglycemia, arthritis, physical or psychological condition caused by stress, or substance addiction in a human; and wherein said composition is obtained at least in part from a leafy and/or immature plant part from one or more monocotyledonous plants selected from the group consisting of corn, wheat, barley, rye, oats, rice, sorghum, millet, bamboo, Job's Tears, barley-like grasses, and wild grasses.

30. A process as defined in claim 29, wherein said composition is obtained at least in part from the leafy part of one or more immature monocotyledonous plants selected from the group consisting of corn, wheat, barley, rye, oats, rice, sorghum, millet, bamboo, Job's Tears, barley-like grasses, and wild grasses, by growing the plant to an immature life history stage and harvesting the plant.

31. A process as defined in claim 1, the process comprising enhancing mood and/or treating a mental or mood disorder caused by stress.

* * * * *

UNITED STATES PATENT AND TRADEMARK OFFICE
CERTIFICATE OF CORRECTION

PATENT NO. : 7,521,468 B2
APPLICATION NO. : 11/385415
DATED : April 21, 2009
INVENTOR(S) : Rosenfeld et al.

It is certified that error appears in the above-identified patent and that said Letters Patent is hereby corrected as shown below:

Title Page
Page 2, left column, Item 56, Other Publications, change "Frandsen et al. "Maternal transfer of the 6-MBOA chemical signal in Microtus montarius during gestation and lactation," Canadian Journal of Zoology, 71: 1799-1803, 1993." to --Frandsen et al. Maternal transfer of the 6-MBOA chemical signal in Microtus montanus during gestation and lactation," Canadian Journal of Zoology, 71: 1799-1803, 1993.--

Column 12
Line 27, add --,-- after "phase"

Column 15
Line 48, change "Lilidae" to --*Lilidae*--
Line 50, change "Alismataceae" to --*Alismataceae*--
Line 50, change "Araceae" to --*Araceae*--
Line 51, change "Butomaceae, Cyperaceae" to --*Butomaceae, Cyperaceae*--
Line 53, change "Dioscoreaceae" to --*Dioscoreaceae*--
Line 53, change "Hydrocharitaceae" to --*Hydrocharitaceae*--
Line 54, change "Iridaceae" to --*Iridaceae*--
Line 54, change "Juncaceae" to --*Juncaceae*--
Line 55, change "Juncaginaceae, Lemnaceae" to --*Juncaginaceae, Lemnaceae*--
Line 55, change "Liliaceae" to --*Liliaceae*--
Line 56, change "Orchidaceae" to --*Orchidaceae*--
Line 56, change "Poaceae" to --*Poaceae*--
Line 57, change "Graminae), Potamogetonaceae" to --*Graminae), Potamogetonaceae*--
Line 58, change "Sparganiaceae" to --*Sparganiaceae*--
Line 58, change "Typhaceae" to --*Typhaceae*--
Line 59, change "Zosteraceae" to --*Zosteraceae*--
Line 64, change "Cyperaceae and Poaceae" to --*Cyperaceae* and *Poaceae*--
Line 65, change "Graminae)." to --*Graminae*).--

Column 16
Line 60, change "1.20-.mu.g" to --1.20- µg--

Column 17
Line 29, change "(Cervidae)" to --(*Cervidae*)--

UNITED STATES PATENT AND TRADEMARK OFFICE
CERTIFICATE OF CORRECTION

PATENT NO. : 7,521,468 B2
APPLICATION NO. : 11/385415
DATED : April 21, 2009
INVENTOR(S) : Rosenfeld et al.

It is certified that error appears in the above-identified patent and that said Letters Patent is hereby corrected as shown below:

Column 19
Line 8, change "belong" to --belonging--
Line 8, change "Lilidae" to --*Lilidae*--

Column 28
Line 10, insert --,-- after "herein"
Line 12, change "to those" to --to those of--
Line 26, insert --,-- after "families"

Column 29
Line 25, change "5 mg." to --15 mg.--

Column 32
Line 27, change "mood disorder" to --mood disorder in said human--

Signed and Sealed this

Twenty-second Day of December, 2009

David J. Kappos
*Director of the United States Patent and Trademark Office*